US011009502B2

(12) United States Patent
Hanson et al.

(10) Patent No.: US 11,009,502 B2
(45) Date of Patent: *May 18, 2021

(54) ECTOPIC OLFACTORY RECEPTORS AND USES THEREOF

(71) Applicant: Aromyx Corporation, Mountain View, CA (US)

(72) Inventors: Chris Hanson, Sunnyvale, CA (US); William Harries, Boulder Creek, CA (US)

(73) Assignee: Aromyx Corporation, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/240,045

(22) Filed: Jan. 4, 2019

(65) Prior Publication Data

US 2019/0293628 A1    Sep. 26, 2019

Related U.S. Application Data

(63) Continuation of application No. 15/927,083, filed on Mar. 21, 2018, now Pat. No. 10,209,239.

(60) Provisional application No. 62/546,188, filed on Aug. 16, 2017.

(51) Int. Cl.
| G01N 33/566 | (2006.01) |
| C12Q 1/02 | (2006.01) |
| C12Q 1/00 | (2006.01) |
| G01N 33/50 | (2006.01) |
| G01N 33/74 | (2006.01) |

(52) U.S. Cl.
CPC ......... *G01N 33/5008* (2013.01); *C12Q 1/005* (2013.01); *C12Q 1/007* (2013.01); *C12Q 1/025* (2013.01); *G01N 33/5023* (2013.01); *G01N 33/566* (2013.01); *G01N 33/74* (2013.01); *G01N 2333/37* (2013.01); *G01N 2333/726* (2013.01); *G01N 2500/04* (2013.01)

(58) Field of Classification Search
CPC .......... G01N 33/5008; G01N 33/5023; G01N 33/566; G01N 33/74; G01N 2333/37; G01N 2333/726; G01N 2500/04; C12Q 1/005; C12Q 1/007; C12Q 1/025
See application file for complete search history.

(56) References Cited

U.S. PATENT DOCUMENTS

| 5,482,835 | A | 1/1996 | King et al. |
| 5,739,029 | A | 4/1998 | King et al. |
| 5,789,184 | A | 8/1998 | Fowlkes et al. |
| 5,876,951 | A | 3/1999 | Fowlkes et al. |
| 6,001,553 | A | 12/1999 | Broach et al. |
| 6,100,042 | A | 8/2000 | Fowlkes et al. |
| 6,159,705 | A | 12/2000 | Trueheart et al. |
| 6,168,927 | B1 | 1/2001 | King et al. |
| 6,251,605 | B1 | 6/2001 | Ostanin et al. |
| 6,255,059 | B1 | 7/2001 | Klein et al. |
| 6,325,475 | B1 | 12/2001 | Hayes et al. |
| 6,355,473 | B1 | 3/2002 | Ostanin et al. |
| 6,504,008 | B1 | 1/2003 | Xu et al. |
| 6,555,325 | B1 | 4/2003 | Oehlen |
| 6,855,550 | B2 | 2/2005 | King et al. |
| 6,864,060 | B1 | 3/2005 | Fowlkes et al. |
| 7,022,513 | B2 | 4/2006 | Xu et al. |
| 7,081,360 | B2 | 7/2006 | Nadkarni et al. |
| 7,090,991 | B2 | 8/2006 | Oehlen |
| 7,105,309 | B2 | 9/2006 | Fowlkes et al. |
| 7,122,305 | B2 | 10/2006 | Klein et al. |
| 7,223,533 | B2 | 5/2007 | Ostanin et al. |
| 7,223,550 | B2 | 5/2007 | Dhanasekaran et al. |
| 7,235,648 | B1 | 6/2007 | Fowlkes et al. |
| 7,250,263 | B2 | 7/2007 | Klein et al. |
| 7,273,747 | B2 | 9/2007 | Manfredi et al. |
| 7,319,009 | B2 | 1/2008 | Klein et al. |
| 7,361,498 | B2 | 4/2008 | Fowlkes et al. |
| 7,416,881 | B1 | 8/2008 | Fowlkes et al. |
| 7,425,445 | B2 | 9/2008 | Matsunami et al. |
| 7,611,854 | B2 | 11/2009 | Fowlkes et al. |
| 7,691,592 | B2 | 4/2010 | Matsunami et al. |
| 7,838,288 | B2 | 11/2010 | Matsunami et al. |
| 7,879,565 | B2 | 2/2011 | Matsunami et al. |
| 8,298,781 | B2 | 10/2012 | Matsunami et al. |
| 9,400,766 | B2 | 7/2016 | Chee et al. |
| 9,611,308 | B2 | 4/2017 | Matsunami et al. |
| 10,209,239 | B1 | 2/2019 | Hanson et al. |
| 2002/0132273 | A1 | 9/2002 | Stryer et al. |

(Continued)

FOREIGN PATENT DOCUMENTS

| EP | 2 031 063 A2 | 3/2009 |
| EP | 2 957 283 A1 | 12/2015 |

(Continued)

OTHER PUBLICATIONS

Fukutani et al, The N-terminal replacement of an olfactory receptor for the development of a yeast-based biomimetic odor sensor, 2011, Biotechnol Bioeng. vol. 109, pp. 205-212.
Fukutani et al, An improved bioluminescence-based signaling assay for odor sensing with a yeast expressing a chimeric . . . , 2012, Biotechnol. Bioeng. vol. 109, pp. 3143-51.
Fukutani et al, Improving the odorant sensitivity of olfactory receptor-expressing yeast with accessory proteins, 2015, Analy Biochem vol. 471, pp. 1-8.
Gendron et al, In vitro discrimination of tumor cell lines with an electronic nose, 2007, Otolaryn Head Neck Surg vol. 137, pp. 269-273.

(Continued)

*Primary Examiner* — Robert S Landsman
(74) *Attorney, Agent, or Firm* — Cooley LLP

(57) ABSTRACT

Biosensors are disclosed for detecting ligand binding at ectopic Olfactory Receptors. Methods of identifying novel ectopic Olfactory Receptors are also disclosed. Ligands for ectopic Olfactory Receptors are disclosed as well as methods for using these ligands to interact with ectopic Olfactory Receptors, including the use of such ligands in the treatment and/or mitigation of disease conditions.

19 Claims, 1 Drawing Sheet

Specification includes a Sequence Listing.

(56) References Cited

U.S. PATENT DOCUMENTS

| | | | |
|---|---|---|---|
| 2004/0101447 | A1 | 5/2004 | Tajima et al. |
| 2004/0235060 | A1 | 11/2004 | Dhanasekaran et al. |
| 2006/0009618 | A1 | 1/2006 | Devauchelle et al. |
| 2007/0191257 | A1 | 8/2007 | Andretta et al. |
| 2008/0299586 | A1 | 12/2008 | Han et al. |
| 2009/0104072 | A1 | 4/2009 | Ando et al. |
| 2011/0059544 | A1 | 3/2011 | Hong et al. |
| 2011/0177964 | A1 | 7/2011 | Broach et al. |
| 2012/0021932 | A1 | 1/2012 | Mershin et al. |
| 2012/0077210 | A1 | 3/2012 | Trowell et al. |
| 2013/0216492 | A1 | 8/2013 | Kato et al. |
| 2014/0324932 | A1 | 10/2014 | Chee et al. |
| 2016/0091470 | A1 | 3/2016 | Gafsou |
| 2017/0242004 | A1 | 8/2017 | Hanson et al. |
| 2019/0194573 | A1 | 6/2019 | Hanson et al. |
| 2019/0194574 | A1 | 6/2019 | Hanson et al. |
| 2020/0003774 | A1 | 1/2020 | Hanson et al. |

FOREIGN PATENT DOCUMENTS

| | | |
|---|---|---|
| WO | WO 2000070343 | 11/2000 |
| WO | WO 2001027158 | 4/2001 |
| WO | WO-02/068473 A1 | 9/2002 |
| WO | WO-2005/051984 A2 | 6/2005 |
| WO | WO-2005/051984 A3 | 6/2005 |
| WO | WO-2007/121512 A1 | 11/2007 |
| WO | WO 2014165818 | 10/2014 |
| WO | WO-2015/102541 A1 | 7/2015 |
| WO | WO 2016030378 | 3/2016 |
| WO | WO 2017147323 | 8/2017 |

OTHER PUBLICATIONS

Hanson et al, Electronic nose prediction of a clinical pneumonia score; biosensors and microbes, 2005, Anesthesiol. vol. 102, pp. 63-68.

Hashi et al, Modifying expression modes of human neurotensin receptor type I alters sensing capabilities for agonists in yeast . . . , 2018, Biotechnol J vol. 13, 1700522.

Hockstein et al, Correlation of pneumonia score with electronic nose signature: a prosepective study, 2005, Annals Ontol Rhinol Larynol vol. 114, pp. 504-508.

Miranda-Lopez et al, Latest developments in the analysis of aroma compounds, 2006, Adv Agricul Food Biotechnol pp. 175-192.

Misawa et al, Membrane protein-based biosensors, 2018, J. R. Soc. Interface vol. 15, 20170952.

Pajot-Augy et al, Engineered yeasts reporter systems for odorant detection, 2003, J. Recept Signal Transduct vol. 23, pp. 155-171.

Zhao et al, Functional expression of a mammalian odorant receptor, 1998, Science vol. 279, pp. 237-242.

Abaffy, Human olfactory receptors expression and their role in non-olfactory tissues, 2015, J. Pharmacogen Pharmacoproteomics vol. 6, pp. 152-159.

Busse et al., a synthetic sandalwood odorant induces wound-healing processes in keratinocytes via . . . , 2014, J. Invest. Dermatol. vol. 134, pp. 2823-2832.

Flegel et al., Expression profile of ectopic olfactory receptors determined by deep sequencing, 2013, PLoS One 8:e55368.

Ferrer et al., Olfactory receptors in non-chemosensory organs: the nervous system in health and disease, 2016, Front Aging Neurosci vol. 8, article 163.

Kamoun et al., A review on polymeric hydrogel membranes for wound dressing applications: PVA base hydrogel dressings, 2017, J. Adv Res vol. 8, pp. 217-233.

Pavan et al., Potential therapeutic effects of odorants through their ectopic receptors in pigmented cells, 2017, Drug Disc Today (manuscript).

Saito et al., RTP Family Members Induce Functional Expression of Mammalian Odorant Receptors, 2004, Cell vol. 119, pp. 679-691.

Wu et al., Receptor-transporting protein 1 short (RTP1S) mediates translocation and activation of odorant receptors by acting . . . , 2012, J. Biol. Chem. vol. 287, pp. 22287-94.

Zhuang et al., Synergism of accessory factors in functional expression of mammalian odorant receptors, 2007, J. Biol. Chem. vol. 282, pp. 15284-93.

Sasuga et al, The reporter system for GPCR assay with the fission yeast Schizosaccharomyces pombe, 2012, Scientifica vol. 2012, p. 674256.

Dewitt, N. et al., GPCR Biosensor Chip, 1999, Nature Biotechnology vol. 17, pp. 1051.

Gelis, L., et al., Functional characterization of the odorant receptor 51E2 human melanocytes, 2016, J. Biol. Chem. vol. 291, pp. 17772-17786.

Jovancevic, N. et al., Medium chain fatty acids modulate myocardial function via a cardiac odorant receptor, 2017, Basic Res. Cardiol. vol. 112, pp. 13.

Martins, SAF, 2012, Trends in Biotechnology vol. 30, pp. 566-574.

Munakata, Y. et al., Olfactory receptors are expressed in pancreatic B-cells and promote glucose-stimulated insulin secretion, 2018, Scien. Reports vol. 8, pp. 1499.

Yamanaka, M., 2013, 17th International Conference on Miniaturized Systems for Chemistry an dLife Sciences, pp. 398-400.

Mainland et al, Human olfactory receptor responses to odorants, 2015, Scientific Data vol. 2, p. 150002.

Snider et al, Detecting interactions with membrane proteins using a membrane two-hybrid assay in yeast, 2010, Nat Protocol vol. 5, pp. 1281-1293.

Suter et al, Development and application of a DNA microarray-based yeast two-hybrid system, 2013, Nucl Acids Res vol. 41, pp. 1496-1507.

Greenwood, You Smell Sick: Scientists are racing to create tests that can identify illness via odors in patients sweat, breadth and urine, 2016, Scient Am Mind vol. 27, pp. 5.

Final Office Action dated Mar. 13, 2019, for U.S. Appl. No. 15/441,062, filed Feb. 23, 2017, 7 pages.

Final Office Action dated Oct. 17, 2018, for U.S. Appl. No. 15/935,025, filed Mar. 25, 2018, 14 pages.

International Search Report dated May 8, 2017, for PCT application No. PCT/US2017/019179, filed on Feb. 23, 2017, 3 pages.

International Search Report dated Dec. 7, 2018, for PCT application No. PCT/US2018/046636, filed on Aug. 14, 2018, 5 pages.

International Search Report dated May 1, 2019, for PCT application No. PCT/US2018/066430, filed on Dec. 19, 2018, 4 pages.

Minic, J. et al. (2004). "Functional expression of olfactory receptors in yeast and development of a bioassay for odorant screening," FEBS J. 272:524-537.

Non-Final Office Action dated Aug. 24, 2018, for U.S. Appl. No. 15/441,062, filed Feb. 23, 2017, 13 pages.

Non-Final Office Action dated Jun. 11, 2018, for U.S. Appl. No. 15/927,083, filed Mar. 21, 2018, 10 pages.

Non-Final Office Action dated Sep. 27, 2019, for U.S. Appl. No. 15/441,062, filed Feb. 23, 2017, 8 pages.

Non-Final Office Action dated May 21, 2018, for U.S. Appl. No. 15/935,025, filed Mar. 25, 2018, 11 pages.

Notice of Allowance dated Dec. 13, 2018, for U.S. Appl. No. 15/927,083, filed Mar. 21, 2018, 10 pages.

Sasuga, S. et al. (2012). "The Reporter System for GPCR Assay with the Fission Yeast Schizosaccharomyces pombe," Scientifica, pp. 1-11.

Written Opinion of the International Searching Authority dated May 8, 2017, for PCT application No. PCT/US2017/019179, filed on Feb. 23, 2017, 6 pages.

Written Opinion of the International Searching Authority dated Dec. 7, 2018, for PCT application No. PCT/US2018/046636, filed on Aug. 14, 2018, 6 pages.

Written Opinion of the International Searching Authority dated May 1, 2019, for PCT application No. PCT/US2018/066430, filed on Dec. 19, 2018, 5 pages.

Final Office Action dated Jun. 10, 2020, for U.S. Appl. No. 15/441,062, filed Feb. 23, 2017, 11 pages.

Foussat, A. (2015). "La digitalisation des odeurs et du gout transforme la R&D de l'agroalimentaire," The digitalization of smells and

(56) References Cited

OTHER PUBLICATIONS tastes is transforming agri-food R&D, with English translation, located at https://web.archive.org/web/20151225203244/http://www.atelier.net:80/trends/articles/digitalisation-odeurs-gout-transforme-rd-de-agroalimentaire_439265#main, 4 total pages.

Glatz, R. et al. (2011). "Mimicking nature's noses: From receptor deorphaning to olfactory biosensing," Progress in Neurobiology 93:270-296.

Hallem, E.A. et al. (2006). "Insect odor and taste receptors," Annu. Rev. Entomol. 51:113-135.

Ko, H.J. et al. (2010). "Specificity of odorant-binding proteins: A factor influencing the sensitivity of olfactory receptor-based biosensors," Bioprocess Biosyst. Eng. 33:55-62.

Non-Final Office Action dated Nov. 13, 2020, for U.S. Appl. No. 16/572,351, filed Sep. 16, 2019, 9 pages.

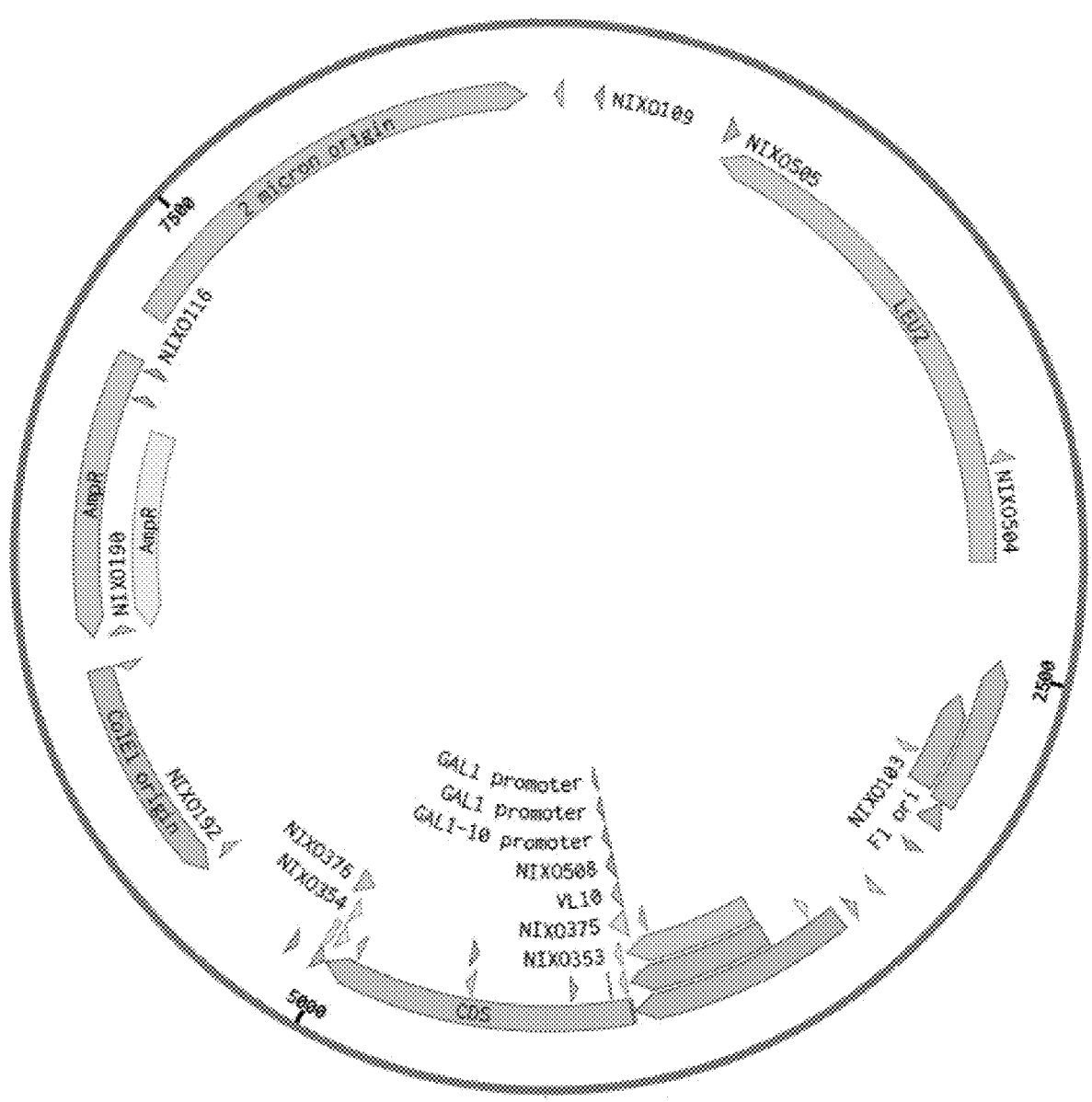

ECTOPIC OLFACTORY RECEPTORS AND USES THEREOF

CROSS-REFERENCE TO RELATED APPLICATIONS

This application is a continuation of U.S. application Ser. No. 15/927,083 filed Mar. 21, 2018, now issued as U.S. Pat. No. 10,209,239, which claims the benefit of U.S. Provisional Application Ser. No. 62/546,188, filed Aug. 16, 2017, each of which is hereby incorporated by reference in its entirety.

The official copy of the Sequence Listing is submitted concurrently with the specification as an ASCII formatted text file via EFS-Web, with a file name of "ARX013_ST25.txt", a creation date of Feb. 26, 2018, and a size of 45 kilobytes. The Sequence Listing filed via EFS-Web is part of the specification and is incorporated in its entirety by reference herein.

BACKGROUND OF THE INVENTION

The olfactory receptor genes have been characterized through homology as seven transmembrane domain G protein-coupled receptors (GPCR). It is estimated that there are probably 500-750 olfactory receptor gene sequences in humans, while there are 500-1000 olfactory genes in rat and mouse. Olfactory receptors are concentrated on the surface of the mucus coated cilia and odorant molecules bind to the olfactory receptors in the olfactory epithelium. Since mammals can detect at least 10,000 odors and there are approximately 1,000 or fewer olfactory receptors, many odorants must interact with multiple olfactory receptors.

The discriminatory power of olfactory receptors is such that it can perceive thousands of volatile chemicals as having different odors. It is known that the olfactory system uses a combinatorial receptor coding scheme to decipher the odor molecules. One olfactory receptor can recognize multiple odorants and one odorant is recognized by multiple olfactory receptors. A slight structural change in the odorant or a change in the concentration of the odorant in the environment results in a change in the odor-code of these receptors.

Odor molecules belong to a variety of chemical classes: from alcohols, aldehydes, ketones and carboxylic acids to sulphur-containing compounds and essential oils. The physicochemical descriptors of odor molecules play an important role in the prediction of odor response by the olfactory receptor. Similar olfactory receptor sequences can have a structural bias for ligand specificity on the basis of the number of carbon atoms present in the ligands. About 8000 odorants have been identified in food. About 400 food odorants have been characterized and this number approximately equals the number of olfactory receptors found in humans. The response of mixtures of odorants is neither the additive nor an average of its components. Some mixtures lead to the emergence of novel perceptual qualities that were not present in the individual components.

Olfactory receptors have been found in non-olfactory tissues such as, for example, adipose tissue, adrenal glands, brain, breast, colon, white blood cells, the gut, heart, kidney, liver, lung, lymph nodes, ovary, placenta, prostate, skeletal muscle, testis and thyroid. ORs expressed in these non-olfactory cells can be referred to as ectopic ORs. In olfactory neurons, only one allele of an OR gene is expressed per neuron. In contrast, non-olfactory cells multiple OR genes can be expressed in each cell. Some ectopic ORs are evolutionarily conserved across mammals, and several ectopic ORs are broadly expressed across many different cell types in mammals.

SUMMARY OF THE INVENTION

In an aspect, biosensors for the detection of interactions at ectopic Olfactory Receptors are provided herein. These biosensors can be used to identify agonists and antagonists of the ectopic Olfactory Receptors. A plurality of biosensors can be used to detect the interaction of ligand(s) at a plurality of ectopic Olfactory Receptors. In an aspect, the plurality of biosensors can represent the repertoire or a portion of the repertoire of the ectopic Olfactory Receptors found on a particular type of cell and/or tissue. For example, the plurality of biosensors can represent the repertoire or a portion of the repertoire of ectopic Olfactory Receptors expressed on skin, brain, breast, colon, heart, kidney, liver, ovary, prostate, testis, white blood cells, lymph nodes, or other cells and tissue in a subject. The plurality of biosensors can represent the repertoire or a portion of the repertoire of ectopic Olfactory Receptors expressed on skin including, for example, the Olfactory Receptor OR2AT4. The plurality of biosensors can represent the repertoire or a portion of the repertoire of ectopic Olfactory Receptors expressed on dopaminergic neurons including, for example, OR51E1, OR51E2, and OR2J3.

The biosensors may also include a G-protein complex and an adenylate cyclase. The G-protein complex can be comprised of three subunits the Gα subunit, Gβ subunit, and Gγ subunit. The adenylate cyclase and the G protein complex can be derived from the same species. Alternatively, the adenylate cyclase and the G protein complex can be derived from different species. The G protein subunits also can be derived from the same or from different species. The biosensor polypeptides include polypeptides that have 70%, 80%, 90%, 95%, and 99% sequence homology with an ectopic Olfactory Receptor.

The biosensor can have a dynamic range of six to seven orders of magnitude, and the biosensor can detect binding of odorants and other molecules in a range of 0.15 parts per billion to about 420,000 parts per billion, or $10^{-9}$ M to about $10^{-3}$ M. The window of detection of a biosensor can be six to seven orders of magnitude within the range of 10 M to $10^{-12}$ M. The biosensor may also detect binding of odorants and other molecules in a range of $10^{-11}$ M to about $10^{-2}$ M. The window of detection of the biosensor can be nine to ten orders of magnitude within the range of 10 M to $10^{-12}$ M. The biosensors can also have a window of detection of three to five orders of magnitude within the range of 10 M to $10^{-12}$ M. The biosensor can have a window of detection of 1, 2, 3, 4, 5, 6, 7, 8, 9, or 10 orders of magnitude.

Nucleic acids encoding the biosensors are also disclosed in the description. These nucleic acids include nucleic acids that hybridize under stringent hybridization conditions to nucleic acids encoding one of the biosensor polypeptides. The biosensor polypeptides include the polypeptides encoded by nucleic acids that hybridize under stringent hybridization conditions to nucleic acids encoding the biosensor polypeptides describe herein. The nucleic acids encode a polypeptide of an ectopic Olfactory Receptor, or are a nucleic acid that hybridizes under stringent hybridization conditions to a nucleic acid encoding an ectopic Olfactory Receptor. The nucleic acids can encode a polypeptide that has 70%, 80%, 90%, 95%, and 99% sequence identity with an ectopic Olfactory Receptor.

The description also discloses biosensor polypeptides and biosensor nucleic acids contained within host cells. The host cells can be eukaryotic cells, such as, for example, a fungal cell, animal cell, plant cell, or algae cell. The fungal cell can be selected from *Saccharomyces, Pichia, Aspergillus, Chrysosporium*, or *Trichoderma*. The fungal cell can be *Saccharomyces cerevisiae, Pichia pastoris, Aspergillus niger, Aspergillus oryzae, Chrysosporium lucknowense*, or *Trichoderma reesei*. The host cell can be a mammalian cell line derived from Chinese hamster cells, Human kidney cells, Monkey kidney cells, Human cervical cancer cells, or Mouse myeloma cells. The host cell can be a human cell. The host cell can be a murine cell. The host cell can be a canine cell.

Uses of host cells containing the biosensor polypeptide and biosensor nucleic acids are also described herein. Membrane fractions and uses of membrane fractions derived from host cells with biosensor are described. A reference receptor-reporter can be included in the host cell or membrane fraction to allow relative, real-time measurements to be made on the biosensor. Real time measurements can be used to measure the interaction of a ligand with at least one ectopic Olfactory Receptor. Real time measurements can be used to measure the interaction of a ligand at a plurality of different ectopic Olfactory Receptors. Real time measurements can be made and compared to a reference to provide comparative numbers for the interaction of a ligand at ectopic Olfactory Receptors. The reporter monitored in real time can be an optical reporter or a nonoptical reporter. The reference receptor can be associated with a reporter that is different from the reporter associated with the ectopic Olfactory Receptor(s). The different reporters can be optical reporters.

In other aspects, the disclosure relates to new ectopic Olfactory Receptors and methods for finding new ectopic Olfactory Receptors. High throughput screening of RNA (sequencing) from different tissues/cells can identify new ectopic Olfactory Receptors that are expressed in the tissue/cells. These high throughput screenings can also be used to compare diseased and healthy tissue/cells to identify ectopic Olfactory Receptors that are associated with disease, abnormal states, or damaged states.

In an aspect, ligands for ectopic Olfactory Receptors can be used to interact with an ectopic Olfactory Receptor. The ligand can be an agonist or antagonist of the ectopic Olfactory Receptor. A plurality of ligands can be used to interact with a plurality of ectopic Olfactory Receptors on the cells of a certain tissue including for example, skin, brain, breast, colon, heart, kidney, liver, ovary, prostate, testis, white blood cells or lymph nodes. Ligands can be antibodies, other polypeptides, small peptides, and/or small molecules.

In an aspect, ligands for ectopic Olfactory Receptors can be used in therapies for a subject. Such ligands include, for example, antibodies that bind to the ectopic Olfactory Receptor. The ligands can be used to stimulate cells to become active during wound healing (e.g., skin cells including stem cells), bone repair (periosteal and chondroblast cells), organ repair, and nerve regeneration for example, during limb reattachment, and neural stem cell growth and differentiation. Ligands for ectopic Olfactory Receptors can also be used in treatments for Parkinson's, melanoma and other cancers. Ligands for ectopic Olfactory Receptors also can be used to inhibit angiogenesis (in cancer) or to induce angiogenesis (in organ and tissue repair). Ligands for ectopic Olfactory Receptors can be used for contraception or in fertility treatments. Ligands for ectopic Olfactory Receptors can be used to induce chemotaxis or alter cellular activity of target cells.

BRIEF DESCRIPTION OF THE FIGURES

FIG. 1 depicts a plasmid map for an OR biosensor construct.

DETAILED DESCRIPTION OF THE INVENTION

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Definitions

As used herein, an "agonist" is defined to be any molecule which binds to a receptor on a cell, which receptor binding can potentially lead to subsequent changes in the cell's functions. When agonist binds to a sufficient number of receptors, the receptors activate processes in the cell.

As used herein, an "antagonist" is defined to be any molecule which binds to a receptor on a cell and inhibits the receptor from activating processes in the cell. This inhibition can include competitive binding against agonists (when an antagonist is bound agonists cannot bind to the receptor) and allosteric effects (when the antagonist binds agonists can still bind the receptor but cannot activate the receptor).

As used herein, an "antibody" is defined to be a protein functionally defined as a ligand-binding protein and structurally defined as comprising an amino acid sequence that is recognized by one of skill as being derived from the variable region of an immunoglobulin. An antibody can consist of one or more polypeptides substantially encoded by immunoglobulin genes, fragments of immunoglobulin genes, hybrid immunoglobulin genes (made by combining the genetic information from different animals), or synthetic immunoglobulin genes. The recognized, native, immunoglobulin genes include the kappa, lambda, alpha, gamma, delta, epsilon and mu constant region genes, as well as myriad immunoglobulin variable region genes and multiple D-segments and J-segments. Light chains are classified as either kappa or lambda. Heavy chains are classified as gamma, mu, alpha, delta, or epsilon, which in turn define the immunoglobulin classes, IgG, IgM, IgA, IgD and IgE, respectively. Antibodies exist as intact immunoglobulins, as a number of well characterized fragments produced by digestion with various peptidases, or as a variety of fragments made by recombinant DNA technology. Antibodies can derive from many different species (e.g., rabbit, sheep, camel, human, or rodent, such as mouse or rat), or can be synthetic. Antibodies can be chimeric, humanized, or humaneered. Antibodies can be monoclonal or polyclonal, multiple or single chained, fragments or intact immunoglobulins.

As used herein, an "antibody fragment" is defined to be at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', F(ab')$_2$, and Fv fragments, scFv antibody fragments, linear antibodies, single domain antibodies such as sdAb (either $V_L$ or $V_H$), camelid VHH domains, and multi-specific antibodies formed from antibody fragments. The term "scFv" is defined to be a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the $V_L$ and $V_H$ variable regions in either order, e.g., with respect to the N-terminal and C-terminal ends of the polypeptide, the scFv may comprise $V_L$-linker-$V_H$ or may comprise $V_H$-linker-$V_L$.

As used herein, a "modified antibody" is defined as an antibody fragment (enzymatic or recombinant), chimeric antibody, humanized antibody, humaneered antibody, single chain antibody, diabody, other recombinant antibody that is different in structure from a native antibody, or an antibody that has modification(s) (post-translational or made in situ by chemical modification) that are non-natural and not present on the native antibody.

As used herein, an "antigen" is defined to be a molecule that provokes an immune response. This immune response may involve either antibody production, or the activation of specific immunologically-competent cells, or both. The skilled artisan will understand that any macromolecule, including, but not limited to, virtually all proteins or peptides, including glycosylated polypeptides, phosphorylated polypeptides, and other post-translation modified polypeptides including polypeptides modified with lipids, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. An antigen may be encoded by a partial nucleotide sequence of one or more gene(s) and that these nucleotide sequences can be arranged in various combinations to encode polypeptides that elicit a desired immune response. Moreover, a skilled artisan will understand that an antigen need not be encoded by a "gene" at all. Antigen can be synthesized or can be derived from a biological sample, or can be a macromolecule besides a polypeptide. Such a biological sample can include, but is not limited to a tissue sample, a tumor sample, a cell or a fluid with other biological components.

As used herein, an "aromagraph" refers to a digital representation of the response to a ligand by a repertoire of Olfactory Receptors, including ectopic Olfactory Receptors.

As used herein, an "ectopic Olfactory Receptor" is an Olfactory Receptor that is located in organs, tissue, and/or cells that are not part of the chemosensory organs responsible for olfaction.

As used herein, an "effective amount" refers to an amount of a compound, formulation, material, or composition, as described herein effective to achieve a particular biological result.

As used herein, the terms "express" or "expression" refer to the production of a protein product from the genetic information contained within a nucleic acid sequence.

As used herein, an "expression vector" and an "expression construct" are used interchangeably, and are both defined to be a plasmid, virus, or other nucleic acid designed for protein expression in a cell. The vector or construct is used to introduce a gene into a host cell whereby the vector will interact with polymerases in the cell to express the protein encoded in the vector/construct. The expression vector and/or expression construct may exist in the cell extrachromosomally or integrated into the chromosome. When integrated into the chromosome the nucleic acids comprising the expression vector or expression construct will remain an expression vector or expression construct.

As used herein, the term "fusion protein" and "fusion polypeptide" are used interchangeably and both refer to two or more nucleotide sequences obtained from different genes that have been cloned together and that encode a single polypeptide segment. Fusion proteins are also referred to as "hybrid proteins" or "chimeric proteins." As used herein, the term "fusion protein" includes polypeptide coding segments that are obtained from different species, as well as coding segments that are obtained from the same species.

As used herein, the term "heterologous" when used with reference to portions of a polynucleotide indicates that the nucleic acid comprises two or more subsequences that are not normally found in the same relationship to each other in nature. For instance, a nucleic acid is typically recombinantly produced, having two or more sequences, e.g., from unrelated genes arranged to make a new functional nucleic acid. Similarly, a "heterologous" polypeptide or protein refers to two or more subsequences that are not found in the same relationship to each other in nature.

As used herein, the term "host cell" refers to a prokaryotic or eukaryotic cell into which vectors or constructs may be introduced, expressed and/or propagated. A microbial host cell is a cell of a prokaryotic or eukaryotic microorganism, including bacteria, yeasts, microscopic fungi and microscopic phases in the life-cycle of fungi and slime molds. Typical eukaryotic host cells are yeast or filamentous fungi, or mammalian cells, such as Chinese hamster cells, murine NIH 3T3 fibroblasts, human kidney cells, or rodent myeloma or hybridoma cells.

As used herein, the term "isolated" refers to a nucleic acid or polypeptide separated not only from other nucleic acids or polypeptides that are present in the natural source of the nucleic acid or polypeptide, but also from other cellular components, and preferably refers to a nucleic acid or polypeptide found in the presence of (if anything) only a solvent, buffer, ion, or other component normally present in a solution of the same. The terms "isolated" and "purified" do not encompass nucleic acids or polypeptides present in their natural source.

As used herein, the term "mammal" refers to warm-blooded vertebrate animals all of which possess hair and suckle their young.

As used herein, an "odorant" refers to any substance that can be detected by at least one Olfactory Receptor.

As used herein, "olfaction" or "olfactory reception" refers to the detection of compounds by an Olfactory Receptor coupled to a cell signaling pathway. The compound detected is termed an "odorant" and may be air-borne (i.e., volatile) and/or in solution.

As used herein, the terms "Olfactory Receptor" or "OR" are used interchangeably herein to refer to olfactory receptors, trace amine associated receptors, vomeronasal receptors, formyl peptide receptors, membrane guanylyl cyclase, subtype GC-D receptors, and G-protein coupled taste receptors. Olfactory Receptors include hybrid receptors made from olfactory receptors, trace amine associated receptors, vomeronasal receptors, formyl peptide receptors, membrane guanylyl cyclase, subtype GC-D receptors, and G-protein coupled taste receptors.

As used herein, "percentage of sequence identity" and "percentage homology" are used interchangeably herein to refer to comparisons among polynucleotides or polypeptides, and are determined by comparing two optimally aligned sequences over a comparison window, where the portion of the polynucleotide or polypeptide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, *Adv Appl Math*. 2:482, 1981; by the homology alignment algorithm of Needleman and Wunsch, *J Mol Biol*. 48:443, 1970; by the search for similarity method of Pearson and Lipman, *Proc Natl Acad Sci. USA* 85:2444, 1988; by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Greene Publishing Associates, Inc. and John Wiley & Sons, Inc., (1995 Supplement). Examples of algorithms that are suitable for determining percent sequence identity and sequence similarity are the BLAST and BLAST 2.0 algorithms, which are described in Altschul et al., *J. Mol. Biol*. 215:403-410, 1990; and Altschul et al., *Nucleic Acids Res*. 25(17):3389-3402, 1977; respectively. Software for performing BLAST analyses is publicly available through the National Center for Biotechnology Information website. BLAST for nucleotide sequences can use the BLASTN program with default parameters, e.g., a wordlength (W) of 11, an expectation (E) of 10, M=5, N=-4, and a comparison of both strands. BLAST for amino acid sequences can use the BLASTP program with default parameters, e.g., a wordlength (W) of 3, an expectation (E) of 10, and the BLOSUM62 scoring matrix (see Henikoff and Henikoff, *Proc Natl Acad Sci. USA* 89:10915, 1989). Exemplary determination of sequence alignment and % sequence identity can also employ the BESTFIT or GAP programs in the GCG Wisconsin Software package (Accelrys, Madison Wis.), using default parameters provided.

As used herein, the terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, PEGylation or any other manipulation or modification, such as conjugation with a labeling or bioactive component.

As used herein, the term "purified" means that the indicated nucleic acid or polypeptide is present in the substantial absence of other biological macromolecules, e.g., polynucleotides, proteins, and the like. The polynucleotide or polypeptide can be purified such that it constitutes at least 95% by weight, more preferably at least 99.8% by weight, of the indicated biological macromolecules present (but water, buffers, and other small molecules, especially molecules having a molecular weight of less than 1000 daltons, can be present).

As used herein, the term "real time" refers to taking multiple measurements during a reaction or interaction as opposed to making a single measurement at the end of the reaction, or at a specified time point. Real time measurements are often used to quantitate the amount of a component in a sample, or to provide relative quantification of two or more components in a sample. Real time measurements can also be used to determine kinetic parameters of a reaction or interaction.

As used herein, the term "recombinant nucleic acid" refers to a nucleic acid in a form not normally found in nature. For example, a recombinant nucleic acid may be flanked by a nucleotide sequence not naturally flanking the nucleic acid or the recombinant nucleic acid may have a sequence not normally found in nature. Recombinant nucleic acids can be originally formed in vitro by the manipulation of nucleic acid by restriction endonucleases, or alternatively using such techniques as polymerase chain reaction. It is understood that once a recombinant nucleic acid is made and reintroduced into a host cell or organism, it may replicate non-recombinantly, i.e., using the in vivo cellular machinery of the host cell rather than in vitro manipulations; however, such nucleic acids, once produced recombinantly, although subsequently replicated non-recombinantly, are still considered recombinant.

As used herein, the term "recombinant polypeptide" refers to a polypeptide expressed from a recombinant nucleic acid, or a polypeptide that is chemically synthesized in vitro.

As used herein, the term "recombinant variant" refers to any polypeptide differing from naturally occurring polypeptides by amino acid insertions, deletions, and substitutions, created using recombinant DNA techniques. Guidance in determining which amino acid residues may be replaced, added, or deleted without abolishing activities of interest, such as enzymatic or binding activities, may be found by comparing the sequence of the particular polypeptide with that of homologous peptides and minimizing the number of amino acid sequence changes made in regions of high homology.

As used herein, the terms "repertoire" or "library" refers to a library of genes encoding a plurality of different Olfactory Receptors. The repertoire or library can represent all of the Olfactory Receptors of a species, e.g., human, dog, or cat. The repertoire or library can represent the Olfactory Receptors that detect a taste, scent, smell, aroma, and/or odor. The repertoire or library can represent the Olfactory Receptors that detect a desired, pleasing, arousing, or adverse taste, scent, smell, aroma, and/or odor. The repertoire or library can represent the Olfactory Receptors of a class, family, or type.

As used herein, the term "reporter" or "reporter molecule" refers to a moiety capable of being detected indirectly or directly. Reporters include, without limitation, a chromophore, a fluorophore, a fluorescent protein, a luminescent protein, a receptor, a hapten, an enzyme, and a radioisotope.

As used herein, the term "reporter gene" refers to a polynucleotide that encodes a reporter molecule that can be detected, either directly or indirectly. Exemplary reporter genes encode, among others, enzymes, fluorescent proteins, bioluminescent proteins, receptors, antigenic epitopes, and transporters.

As used herein, "stringent hybridization conditions" refers to hybridizing in 50% formamide at 5×SSC at a temperature of 42° C. and washing the filters in 0.2×SSC at 60° C. (1×SSC is 0.15M NaCl, 0.015M sodium citrate.) Stringent hybridization conditions also encompasses low ionic strength and high temperature for washing, for example 0.015 M sodium chloride/0.0015 M sodium citrate/ 0.1% sodium dodecyl sulfate at 50° C.; hybridization with a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

As used herein, "substantial identity" refers to a polynucleotide or polypeptide sequence that has at least 80 percent sequence identity, at least 85 percent identity and 89 to 95 percent sequence identity. Substantial identity also encompasses at least 99 percent sequence identity as compared to a reference sequence over a comparison window of at least 20 residue positions or a window of at least 30-50 residues, wherein the percentage of sequence identity is calculated by comparing the reference sequence to a sequence that includes deletions or additions or substitutions over the window of comparison. As applied to polypeptides, the term "substantial identity" can mean that two polypeptide sequences, when optimally aligned, such as by the programs GAP or BESTFIT using standard parameters, i.e., default parameters, share at least 80 percent sequence identity, preferably at least 89 percent sequence identity, at least 95 percent sequence identity or more (e.g., 99 percent sequence identity).

Preferably, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

As used herein, "taste receptors" refers to G-protein coupled taste receptors for detecting sweet, bitter, and umami (glutamate), and ion channels and ionotropic receptors for detecting salty and sour.

As used herein, "transfected" or "transformed" or "transduced" are defined to be a process by which an exogenous nucleic acid is transferred or introduced into a host cell. A "transfected" or "transformed" or "transduced" cell is one which has been transfected, transformed or transduced with exogenous nucleic acid. The cell includes the primary subject cell and its progeny.

The singular terms "a", "an", and "the" include plural referents unless context clearly indicates otherwise. Similarly, the word "or" is intended to include "and" unless the context clearly indicates otherwise. Numerical limitations given with respect to concentrations or levels of a substance, such as an antigen, are intended to be approximate. Thus, where a concentration is indicated to be at least (for example) 200 µg, it is intended that the concentration be understood to be at least approximately "about" or "about" 200 µg.

Olfactory Receptors

Ectopic Olfactory Receptors are Olfactory Receptors expressed in organs, tissues and/or cells that do not play a role in olfaction. Ectopic Olfactory Receptors have been found in many non-olfaction tissues and cells including, for example, skin, brain, breast, colon, erythroid cells, eye, heart, kidney, liver, lung, ovary, prostate, spleen, testis, white blood cells, lymph nodes, or other tissues and/or cells in a subject. Ectopic Olfactory Receptors have many roles unrelated to olfaction including, for example, discriminatory chemotaxis in sperm and testes, a wide range of processes during development (e.g., angiogenesis, direction of nerve fibers), regulation of glomerular filtration rate, regulation of actin cytoskeleton and cytokinesis, regulation of blood pressure, and stimulation of cells to secrete polypeptides.

Ectopic Olfactory Receptors found in adipose include, for example, OR51E2, OR2W3, OR51E1, OR2A1/42, OR2A4/ 7, OR52N4, OR13A1, 047D2, OR10J1OR1L8, OR2B6, OR4D6, TAS1R3, TAS2R10, TAS2R13, TAS2R14, TAS2R19, TAS2R20, TAS2R31, TAS2R40, TAS2R42, TAS2R5, VN1R1, and VN1R2. Ectopic Olfactory Receptors found in adrenal tissue include, for example, OR51E2, ORW3, OR51E1, OR2A1/42, OR2A4/7, OR52N4, OR13A1, OR5K2, OR3A2, OR2H2, OR7C1, OR2L13, OR1L8, OR2T8, OR10AD1, OR52B6, OR1E1, OR13J1, OR2C1, OR52D1, OR10A2, OR2B6, OR8G5, OR1F12, OR4D6, TAS1R1, TAS1R3, TAS2R10, TAS2R13, TAS2R14, TAS2R19, TAS2R20, TAS2R3, TAS2R30, TAS2R31, TAS2R4, TAS2R42, TAS2R5, TAS2R50, TAS2R9, and VN1R1. Ectopic Olfactory Receptors found in CNS include, for example, OR51E2, OR2W3, OR4N4, OR51E1, OR52N4, OR13A1, OR5K2, OR7D2, OR3A2, OR2V1, OR2H2, OR7C1, OR2L13, OR1L8, OR2T8, OR10AD1, OR3A3, OR2K2, OR13J1, OR2C1, OR7A5, OR10A2, OR1F12, TAAR3, TAAR5, TAAR6. TAS1R1, TAS1R3, TAS2R1, TAS2R10, TAS2R13, TAS2R14, TAS2R19, TAS2R20, TAS2R3, TAS2R30, TAS2R31, TAS2R39, TAS2R4, TAS2R40, TAS2R42, TAS2R46, TAS2R5, TAS2R50, TAS2R7, TAS2R8, TAS2R9, VN1R1, VN1R2, and VN1R5. Ectopic Olfactory Receptors found in dopaminergic neurons include, for example, OR51E1, OR51E2, and OR2J3. Ectopic Olfactory Receptors found in breast include, for example, OR51E2, OR51E1, OR2A1/42, OR2A4/7, OR52N4, OR5K2, OR3A2, OR2T8, OR10AD1, OR3A3, OR2K2, OR1E1, OR2C1, OR2C3, OR8D1, OR7A5, OR10A2, TAS1R1, TAS1R3, TAS2R10, TAS2R13, TAS2R14, TAS2R19, TAS2R20, TAS2R31, TAS2R4, TAS2R5, and VN1R1. Ectopic Olfactory Receptors found in colon include, for example, OR51E2, OR2W3, OR51E1, OR2A1/42, OR2A4/7, OR5K2, OR7D2, OR7C1, OR2L13, OR7A5, OR51B5, TAS1R1, TAS1R3, TAS2R14, TAS2R20, TAS2R4, TAS2R43, TAS2R5, and VN1R1. Ectopic Olfactory Receptors found in heart include, for example, OR51E2, OR51E1, OR52N4, OR13A1, OR2H2, OR10AD1, OR3A3, OR52B6, OR2K2, OR8G5, OR4D6, TAS1R1, TAS1R3, TAS2R10, TAS2R13, TAS2R14, TAS2R19, TAS2R20, TAS2R3, TAS2R30, TAS2R31, TAS2R4, TAS2R43, TAS2R46, TAS2R5, TAS2R50, TAS2R7, and VN1R1. Ectopic Olfactory Receptors found in kidney include, for example, OR51E2, OR51E1, OR2A1/42, OR2A4/7, OR5K2, OR1L8, OR10A2, OR1F12, TAS1R1, TAS1R3, TAS2R1, TAS2R10, TAS2R14, TAS2R19, TAS2R20, TAS2R3, TAS2R30, TAS2R31, TAS2R4, TAS2R42, TAS2R43, TAS2R5, TAS2R50, and VN1R1. Ectopic Olfactory Receptors found in liver include, for example, OR2W3, OR51E1, OR2A1/42, OR2A4/7, OR7D2, OR1L8, OR2T8. TAS1R3, TAS2R14, TAS2R14, TAS2R20, TAS2R30, TAS2R30, TAS2R40, TAS2R5, VN1R1, and VN1R2. Ectopic Olfactory Receptors found in lymph node include, for example, OR51E2, OR51E1, OR2A1/42, OR52N4, OR13A1, OR5K2, OR3A2, OR2H2, OR3A3, OR2B6, TAS1R3, TAS2R14, TAS2R19, TAS2R20, TAS2R31, TAS2R4, TAS2R40, TAS2R43, TAS2R5, and VN1R1. Ectopic Olfactory Receptors found in lymph node include, for example, OR51E2, OR2W3, OR2A1/42, OR2A4/7, OR52N4, OR5K2, OR7D2, OR52B6, TAS1R1, TAS1R3, TAS2R14, TAS2R20, TAS2R31, TAS2R4, TAS2R5, TAS2R50, and VN1R1. Ectopic Olfactory Receptors found in ovary include, for example, OR51E2, OR2W3, OR4N4, OR51E1, OR2A1/42, OR2A4/7, OR52N4, OR5K2, OR3A2, OR2V1, OR2H2, OR2L13, OR1L8, OR10AD1, OR3A3, OR52B6, OR13J1, OR2C1, OR52D1, OR51B5, OR1F12, TAS1R1, TAS1R3, TAS2R1, TAS2R10, TAS2R13, TAS2R14, TAS2R19, TAS2R20, TAS2R3, TAS2R31, TAS2R4, TAS2R42, TAS2R43, TAS2R5, TAS2R50, TAS2R60, TAS2R7, VN1R1, and VN1R2. Ectopic Olfactory Receptors found in prostate include, for example, OR51E2, OR2W3, OR51E1, OR2A1/42, OR2A4/7, OR52N4, OR13A1, OR5K2, OR2H2, OR7C1, OR1E1, OR13J1, OR51B5, TAS1R3, TAS2R14, TAS2R19, TAS2R20, TAS2R43, TAS2R46, TAS2R5, and VN1R1. Ectopic Olfactory Receptors found in skin include, for example, OR2AT4. Ectopic Olfactory Receptors found in testis include, for example, OR4N4, OR6F1, OR2H1, OR51E2, OR2W3, OR4N4, OR51E1, OR2A1/42, OR2A4/7, OR52N4, OR7D2, OR3A2, OR2V1, OR2H2, OR7C1, OR1OJ1, OR1L8, OR1C1, OR2H1, OR10AD1, OR3A3, OR13C3, OR2K2, OR1E1, OR2C1, OR2K2, OR1E1, OR2C1, OR2C3, OR8D1, OR52D1, OR7A5, OR10A2, OR2B6, OR7E24, OR6F1, OR8G5, OR51B5, OR1F12, TAS1R1, TAS1R3, TAS2R1, TAS2R14, TAS2R19, TAS2R20, TAS2R3, TAS2R31, TAS2R4, TAS2R43, TAS2R5, TAS2R50 TAS2R60, VN1R1, VN1R2, VN1R3, and VN1R4. Ectopic Olfactory Receptors found in white blood cells include, for example, OR2W3, OR2A4/7, OR52N4, OR7D2, OR2L13, OR3A3, OR2C1, OR2C3, OR2B6, TAS1R3, TAS2R14, TAS2R20, TAS2R40, and TAS2R60. Other ectopic Olfactory Receptors found in other tissues, organs and cells are described in Flegel et al., PLoS ONE 8:e55368 (2013), Abaffy, J. Pharmacogen. Pharmacoprot. 6:4 (2015) (dx.doi.org/10.4172/2153-0645.1000152), and Ferrer et al., Front. Aging Neurosci. 8:163 (2016), which are incorporated by reference in their entirety for all purposes.

Most Olfactory Receptors, including ectopic Olfactory Receptors, are G-protein coupled receptors that associate with a G-protein for signal transduction after the receptor is activated by an odorant. GPCRs have a conserved structural feature of seven α-helical transmembrane regions. Most olfactory receptors are about 320±25 amino acids in length. The differences in length mostly result from variations in the N-terminal and C-terminal regions. Most olfactory receptors include the motif MAYDRYVAIC (SEQ ID NO: 1) located at the junction of TM3 (transmembrane section 3) and the intracellular loop between TM3 and TM4. Other motifs conserved in some of the olfactory receptors, include, for example, LHTPMY (SEQ ID NO:2) within the first intracellular loop, FSTCSSH (SEQ ID NO:3) at the beginning of TM6, and PMLNPF (SEQ ID NO:4) in TM7.

Ectopic Olfactory Receptors described herein can be human Olfactory Receptors, or Olfactory Receptors from another mammal, or Olfactory Receptors from another organism. Olfactory Receptors described herein can be hybrid olfactory receptors. Amino acids from the N-terminal region of one Olfactory Receptor can be fused to the N-terminal region of a second, different Olfactory Receptor. The N-terminal amino acids can be from amino acid positions 1-61 of the donor Olfactory Receptor. The N-terminal amino acids can be from amino acid positions 1-55 of the donor Olfactory Receptor. The N-terminal amino acids can be from amino acid positions 1-20 or the amino acids up to the first transmembrane domain, or amino acid positions 1-40 which includes the consensus sequence of the first transmembrane domain. The N-terminal amino acids can be fused to the acceptor Olfactory Receptor at its N-terminal region of amino acid positions 1-61. Amino acids from the C-terminus of a donor polypeptide can be fused to the C-terminal end of the acceptor Olfactory Receptor. 1-50 amino acids from the C-terminus of the acceptor olfactory receptor can be replaced by amino acids from a donor polypeptide. 1-55 amino acids from the C-terminus of the acceptor Olfactory Receptor can be replaced by amino acids from a donor polypeptide. The donor polypeptide can be an Olfactory Receptor.

The acceptor Olfactory Receptor can be a human Olfactory Receptor and the donor Olfactory Receptor can be a human Olfactory Receptor. The acceptor Olfactory Receptor can be a human Olfactory Receptor and the donor Olfactory Receptor can be a murine Olfactory Receptor. The acceptor olfactory receptor can be a human Olfactory Receptor and the donor Olfactory Receptor can be a yeast polypeptide. The acceptor Olfactory Receptor can be a murine Olfactory Receptor and the donor Olfactory Receptor can be a murine Olfactory Receptor. The acceptor Olfactory Receptor can be a murine Olfactory Receptor and the donor Olfactory Receptor can be a human Olfactory Receptor. The acceptor Olfactory Receptor can be a murine Olfactory Receptor and the donor Olfactory Receptor can be a yeast polypeptide. The acceptor Olfactory Receptor can be a canine Olfactory Receptor and the donor Olfactory Receptor can be a canine Olfactory Receptor. The acceptor Olfactory Receptor can be a canine Olfactory Receptor and the donor Olfactory Receptor can be a human or a murine Olfactory Receptor. The acceptor Olfactory Receptor can be a canine Olfactory Receptor and the donor Olfactory Receptor can be a yeast polypeptide.

The amino acids added from the donor Olfactory Receptor can replace the corresponding amino acid positions in the acceptor Olfactory Receptor. The added amino acids from the donor Olfactory Receptor can increase the total number of amino acids in the acceptor Olfactory Receptor. The acceptor Olfactory Receptor can have fewer amino acids (than the starting acceptor Olfactory Receptor) after the fusion is made.

Most mammalian Olfactory Receptors can be classified into two phylogenetic groups, class I and class II Olfactory Receptors. Class I Olfactory Receptors are similar to fish Olfactory Receptors and class II receptors are most characteristic of mammals. In mammals, a majority of the Olfactory Receptors are in class II, but mammals also have class I receptors, for example, humans and mice each have more than 100 class I Olfactory Receptors. The number of olfactory genes varies among mammals from about 800 (including pseudogenes) in primates to about 1,500 in dogs and mice. The number of functional olfactory receptors varies from about 262 in platypus and 390 in humans to 1,284 in rats and 1,194 in mice.

The repertoire of human olfactory receptors includes about 850 genes and pseudogenes, including about 390 putatively functional genes, in 18 gene families, and 300 subfamilies. Databases setting out the organization of the human olfactory receptor genes into families and subfamilies, along with links to the polypeptide and nucleic acid sequences of the olfactory receptors can be found at HUGO Gene Nomenclature Committee website, www.genenames.org/genefamilies/OR, the Olfactory Receptors Database at senselab.med.yale.edu/ORDB/info/humanorseqanal, and HORDE, the Human Olfactory Data Explorer, found at genome.weizmann.ac.il/horde/, all of which are incorporated by reference in their entirety for all purposes.

The repertoire of mouse Olfactory Receptor includes about 1,296 genes and pseudogenes, of which about 80% are putatively functional, in 228 families. Databases with the organization of the mouse Olfactory Receptor genes into families and subfamilies, along with links to the polypeptide and nucleic acid sequences of the olfactory receptors can be found at the Olfactory Receptors Database at senselab.med.yale.edu/ORDB/info/humanorseqanal, which is incorporated by reference in its entirety for all purposes.

The repertoire of canine Olfactory Receptors includes about 1,094 genes. Quignon et al., Genome Biol. vol. 6, pp. R83-R83.9 (2005); Olender et al., Genomics vol. 83, pp. 361-372 (2004); Quignon et al., Chapter 13, CSH Monographs Volume 44: The Dog and Its Genome (2006); which are incorporated by reference in their entirety for all purposes.

The Olfactory Receptor repertoires of other mammals are also within the scope of the invention, including, for example, the Olfactory Receptor repertoires of mice, rats, cats, cows and cattle, horses, goats, pigs, and bears.

A biosensor can be made from human olfactory receptor 1A1 having the amino acid sequence (OR1A1, NCBI 9606, UP000005640, HGNC 8179, NP_055380.2, DMDM 212276451):

```
                                          (SEQ ID NO: 5)
MRENNQSSTL EFILLGVTGQ QEQEDFFYIL FLFIYPITLI

GNLLIVLAIC SDVRLHNPMY FLLANLSLVD IFFSSVTIPK

MLANHLLGSK SISFGGCLTQ MYFMIALGNT DSYILAAMAY

DRAVAISRPL HYTTIMSPRS CIWLIAGSWV IGNANALPHT

LLTASLSFCG NQEVANFYCD ITPLLKLSCS DIHFHVKMMY

LGVGIFSVPL LCIIVSYIRV FSTVFQVPST KGVLKAFSTC

GSHLTVVSLY YGTVMGTYFR PLTNYSLKDA VITVMYTAVT

PMLNPFIYSL RNRDMKAALR KLFNKRISS
```

N-terminal amino acids of the human olfactory receptor 1A1 can be replaced with N-terminal amino acids from the human olfactory receptor 6A2 having the sequence (OR6A2, NCBI 9606, UP000005640, HGNC 15301; NP_003687.2)

```
                                          (SEQ ID NO: 6)
MEWRNHSGRV SEFVLLGFPA PAPLQVLLFA LLLLAYVLVL

TENTLIIMAI RNHSTLHKPM YFFLANMSFL EIWYVTVTIP

KMLAGFVGSK QDHGQLISFE GCMTQLYFFL GLGCTECVLL

AVMAYDRYMA ICYPLHYPVI VSGRLCVQMA AGSWAGGFGI

SMVKVFLISG LSYCGPNIIN HFFCDVSPLL NLSCTDMSTA

ELTDFILAIF ILLGPLSVTG ASYVAITGAV MHIPSAAGRY

KAFSTCASHL TVVIIFYAAS IFIYARPKAL SAFDTNKLVS

VLYAVIVPLL NPIIYCLRNQ EVKRALCCTL HLYQHQDPDP

KKASRNV
```

Amino acids from the N-terminal region of OR6A2 (amino acid positions 1-61) can be fused to OR1A1 to make a fusion olfactory receptor to be used in the biosensor. At least 20 contiguous amino acids from the N-terminal region of OR6A2 can be fused with OR1A1. The N-terminal region of OR6A2 can be amino acid positions 1-55. These amino acids of OR6A2 are fused at a position in the N-terminal region of OR1A1, ranging from 1-61. The N-terminal sequence from OR6A2 can be fused to amino acid position 56 of OR1A1. The human OR6A2 can be used in the biosensor without modification. The human OR6A2 receptor can be modified at its C-terminal end by fusing with other C-terminal sequences from other Olfactory Receptors. The human OR6A2 can be modified at its N-terminal end by fusing N-terminal sequences from other olfactory receptors.

A biosensor can be made from the human olfactory receptor 2J2 (OR2J2, HGNC 8260; NP_112167).

```
                                          (SEQ ID NO: 7)
MMIKKNASSE DFFILLGFSN WPQLEVVLFV VILIFYLMTL

TGNLFIIILS YVDSHLHTPM YFFLSNLSFL DLCYTTSSIP

QLLVNLRGPE KTISYAGCMV QLYFVLALGI TECVLLVVMS
```

```
               -continued
YDRYVAVCRP LHYTVLMHPR FCHLLVAASW VIGFTISALH

SSFTFWVPLC GHRLVDHFFC EVPALLRLSC VDTHANELTL

MVMSSIFVLI PLILILTTYG AIARAVLSMQ STTGLQKVFR

TCGAHLMVVS LFFIPVMCMY LQPPSENSPD QGKFIALFYT

VVTPSLNPLI YTLRNKHVKG AAKRLLGWEW GK
```

A biosensor can be made from the human olfactory receptor 2W1 (OR2W1, HGNC 8281; NP_112165).

```
                                         (SEQ ID NO: 8)
MDQSNYSSLH GFILLGFSNH PKMEMILSGV VAIFYLITLV

GNTAIILASL LDSQLHTPMY FFLRNLSFLD LCFTTSIIPQ

MLVNLWGPDK TISYVGCIIQ LYVYMWLGSV ECLLLAVMSY

DRFTAICKPL HYFVVMNPHL CLKMIIMIWS ISLANSVVLC

TLTLNLPTCG NNILDHFLCE LPALVKIACV DTTTVEMSVF

ALGIIIVLTP LILILISYGY IAKAVLRTKS KASQRKAMNT

CGSHLTVVSM FYGTIIYMYL QPGNRASKDQ GKFLTLFYTV

ITPSLNPLIY TLRNKDMKDA LKKLMRFHHK STKIKRNCKS
```

A biosensor can be made from the human olfactory receptor 5P3 (OR5P3, HGNC 14784; NP_703146).

```
                                         (SEQ ID NO: 9)
MGTGNDTTVV EFTLLGLSED TTVCAILFLV FLGIYVVTLM

GNISIIVLIR RSHHLHTPMY IFLCHLAFVD IGYSSSVTPV

MLMSFLRKET SLPVAGCVAQ LCSVVTFGTA ECFLLAAMAY

DRYVAICSPL LYSTCMSPGV CIILVGMSYL GGCVNAWTFI

GCLLRLSFCG PNKVNHFFCD YSPLLKLACS HDFTFEIIPA

ISSGSIIVAT VCVIAISYIY ILITILKMHS TKGRHKAFST

CTSHLTAVTL FYGTITFIYV MPKSSYSTDQ NKVVSVFYTV

VIPMLNPLIY SLRNKEIKGA LKRELRIKIF S
```

N-terminal amino acids from the rat RI7 olfactory receptor can be fused to the N-terminal end of a human olfactory receptor. The rat RI7 olfactory receptor has the N-terminal sequence:

```
                                         (SEQ ID NO: 10)
MERRNHSGRV SEFVLLGFPA PAPLRVLLFF LSLLAYVLVL

TENMLIIIAI RNHPTLHKPM YFFLANMSFL EIWYVTVTIP

KMLAGFIGSK ENHGQLISFE
```

Amino acid positions 1-55 of the N-terminal sequence of the rat RI7 olfactory receptor can be fused to the N-terminal end of the human olfactory receptor.

The Olfactory Receptor can be fused at its N- or C-terminal end with FLAG or HIS tags to assist in certain purification and biochemical characterizations of the biosensor polypeptides.

Human olfactory receptors can be classified into 18 families: 1, 2, 3, 4, 5, 6, 7, 8, 9, 10, 11, 12, 13, 14, 51, 52, 55 and 56. Family OR1 has 21 members: OR1A, OR1B, OR1C, OR1D, OR1E, OR1F, OR1G, OR1H, OR1I, OR1J, OR1K, OR1L, OR1M, OR1N, OR1P, OR1Q, OR1R, OR1S, OR1X, OR1AA, and OR1AB. Family OR2 has 41 members: OR2A, OR2B, OR2C, OR2D, OR2E, OR2F, OR2G, OR2H, OR2I, OR2J, OR2K, OR2L, OR2M, OR2N, OR2Q, OR2R, OR2S, OR2T, OR2U, OR2V, OR2W, OR2X, OR2Y, OR2Z, OR2AD, OR2AE, OR2AF, OR2AG, OR2AH, OR2AI, OR2AJ, OR2AK, OR2AL, OR2AM, OR2AO, OR2AP, OR2AS, and OR2AT. Family OR3 has 3 members: OR3A, OR3B, and OR3D. Family OR4 has 21 members: OR4A, OR4B, OR4C, OR4D, OR4E, OR4F, OR4G, OR4H, OR4K, OR4L, OR4M, OR4N, OR4P, OR4Q, OR4R, OR4S, OR4T, OR4U, OR4V, OR4W, and OR4X. Family OR5 has 49 members: OR5A, OR5B, OR5C, OR5D, OR5E, OR5F, OR5G, OR5H, OR5I, OR5J, OR5K, OR5L, OR5M, OR5P, OR5R, OR5S, OR5T, OR5V, OR5W, OR5AC, OR5AH, OR5AK, OR5AL, OR5AM, OR5AN, OR5AO, OR5AP, OR5AQ, OR5AR, OR5AS, OR5AU, OR5W, OR5X, OR5Y, OR5Z, OR5BA, OR5BB, OR5BC, OR5BD, OR5BE, OR5BH, OR5BJ, OR5BK, OR5BL, OR5BM, OR5BN, OR5BP, OR5BQ, OR5BR, OR5BS, and OR5BT. Family OR6 has 21 members: OR6A, OR6B, OR6C, OR6D, OR6E, OR6F, OR6J, OR6K, OR6L, OR6M, OR6N, OR6P, OR6Q, OR6R, OR6S, OR6T, OR6U, OR6V, OR6W, OR6X, and OR6Y. Family OR7 has 9 members: OR7A, OR7C, OR7D, OR7E, OR7G, OR7H, OR7K, OR7L, and OR7M. Family OR8 has 18 members: OR8A, OR8B, OR8C, OR8D, OR8F, OR8G, OR8H, OR8I, OR8J, OR8K, OR8L, OR8Q, OR8R, OR8S, OR8T, OR8U, OR8V, and OR8X. Family OR9 has 12 members: OR9A, OR9G, OR9H, OR9J, OR9K, OR9L, OR9M, OR9N, OR9P, OR9Q, OR9R, and OR9S. Family OR10 has 29 members: OR10A, OR10B, OR10C, OR10D, OR10G, OR10H, OR10J, OR10K, ORION, OR10P, OR10Q, OR10OR, OR10S, OR10T, OR10U, OR10V, OR10W, OR10X, OR10Y, OR10Z, OR10AA, OR10AB, OR10AC, OR10AD, OR10AE, OR10AF, OR10AG, OR10AH, and OR10AK. Family OR11 has 11 members: OR11A, OR11G, OR11H, OR11I, OR11J, OR11K, OR11L, OR11M, OR11N, OR11P, OR11Q. Family OR12 has 1 member: OR12D. Family OR13 has 11 members: OR13A, OR13C, OR13D, OR13E, OR13F, OR13G, OR13H, OR13I, OR13J, OR13K, and OR13Z. Family OR14 has 6 members: OR14A, OR14C, OR14I, OR14J, OR14K, and OR14L. Family OR51 has 21 members: OR51A, OR51B, OR51C, OR51D, OR51E, OR51F, OR51G, OR51H, OR51I, OR51J, OR51K, OR51L, OR51M, OR51N, OR51P, OR51Q, OR51R, OR51S, OR51T, OR51V, and OR51AB. Family OR52 has 22 members: OR52A, OR52B, OR52D, OR52E, OR52H, OR52I, OR52J, OR52K, OR52L, OR52M, OR52N, OR52P, OR52Q, OR52R, OR52S, OR52T, OR52U, OR52V, OR52W, OR52X, OR52Y, and OR52Z. Family OR55 has 1 member: OR55B. Family OR56 has 2 members: OR56A and OR56B.

Identification of Novel Ectopic Olfactory Receptors

Sequencing technologies can be used to identify Olfactory Receptors that are expressed in non-olfaction tissues and cells. For example, RNA sequencing (also called whole transcriptome shotgun sequencing) can be used to reveal the temporal presence and quantity of RNA transcripts for ectopic Olfactory Receptors in a wide selection of human tissues including tissues from prenatal, postnatal, childhood, adulthood, and geriatric subjects.

Once a tissue(s) is identified as expressing an ectopic olfactory receptor, knockout experiments in the cell/tissue culture can be used to study the role of the ectopic Olfactory Receptor. Ectopic Olfactory Receptors are involved in, for example, chemotaxis, and facilitating cell-to-cell, cell-to-tissue, or tissue-to-tissue communication. These roles are involved in, for example, development and differentiation of tissues and cells, normal childhood development, puberty related development, and other normal physiological functions.

Cancer cells and cells in other disease states can also be screened for ectopic Olfactory Receptor expression to find aberrantly expressed ectopic Olfactory Receptors. Such aberrant ectopic Olfactory Receptors could be involved in disease processes such as angiogenesis in cancer, or angiogenesis in certain retinal diseases. Such aberrant ectopic Olfactory Receptors can be used diagnostically to identify disease states, and can be targets, for example, of antagonists for inhibiting the disease processes in which the ectopic Olfactory Receptor is involved.

Biosensors

Biosensors for the detection of interactions at an Olfactory Receptor, including ectopic Olfactory Receptors, are described herein. The biosensors can be used to detect the interaction of a ligand at an Olfactory Receptor. A biosensor can comprise a plurality of ectopic Olfactory Receptors and the plurality of Olfactory Receptors can be used to detect a ligand. The plurality of Olfactory Receptors in the biosensor can represent the repertoire or a portion of the repertoire of an animals ectopic Olfactory Receptors found in a particular tissue, tissues, cell or cells. The plurality of Olfactory Receptors in the biosensor can represent the repertoire, a portion of the repertoire of human Olfactory Receptors, or the repertoire of ectopic Olfactory Receptors expressed on a cell or a tissue or tissues. A plurality of ectopic Olfactory Receptors in the biosensor can represent the portion of the repertoire of human Olfactory Receptors found in a neural tissue. A plurality of ectopic Olfactory Receptors in the biosensor can represent the portion of the repertoire of human Olfactory Receptors found in skin cells. A plurality of ectopic Olfactory Receptors in the biosensor can represent the portion of the repertoire of human Olfactory Receptors found in cells of the bone. A plurality of ectopic Olfactory Receptors in the biosensor can represent the portion of the repertoire of human Olfactory Receptors found in tumor cells. A plurality of ectopic Olfactory Receptors in the biosensor can represent the portion of the repertoire of human Olfactory Receptors found in a diseased tissue.

Individual biosensors can be comprised of an Olfactory Receptor, including an ectopic Olfactory Receptor, that is fused in its N-terminal region to a polypeptide sequence that targets the nascent polypeptide to the host cell secretory apparatus for insertion of the Olfactory Receptor into the membrane, and fused in its C-terminal region to a polypeptide that stabilizes the receptor in the membrane. The polypeptide fused to the C-terminal region of the Olfactory Receptor can target the receptor to the outer membrane of the host cell. The Olfactory Receptor can be a mammalian olfactory receptor. The Olfactory Receptor can be a human Olfactory Receptor. A full length Olfactory Receptor can be used in the biosensor. The full length Olfactory Receptor can be a human Olfactory Receptor.

The biosensor can include a G-protein signaling pathway. Many G-protein signaling pathways may be used. The G-protein signaling pathway can comprise the G-protein-mediated activation of adenylate cyclase with resultant production of cAMP as a second messenger. The cAMP can interact with a cAMP activated cation channel.

The biosensors can also be comprised of a G-protein and an adenylate cyclase (e.g., Uniprot O60266). The G-protein can be comprised of three subunits the $G\alpha$ subunit (e.g., Uniprot P38405), $G\beta$ subunit (e.g., Uniprot P62879) and $G\gamma$ subunit (e.g., Uniprot P63218). The adenylate cyclase and the G protein can be from the same species. The adenylate cyclase and the G protein can be from different species. The G protein subunits can be from the same or from different species. The Olfactory Receptor, G protein and adenylate cyclase can be from the same species, or one or more of the components are from different species. The Olfactory Receptor and G protein of the biosensor can originate from human polypeptides.

The biosensor can include a reporter. The G proteins of the biosensor can interact directly with a reporter polypeptide to produce a detectable signal, e.g., adenylate cyclase is a reporter polypeptide that produces cAMP. The cAMP molecule itself can be detected (e.g., commercially available kits are sold by, for example, Thermofisher Scientific, Ray Biotech, Enzo Life Sciences, Cayman Chemical, and Cell BioLabs). The G proteins of the biosensor can interact with a polypeptide that induces a reporter. The G proteins can interact with a polypeptide (e.g., adenylate cyclase) to create a first signal, and a second system amplifies the first signal when the reporter responds to the first signal. Multiple amplification steps can be used to increase detection of interactions at the Olfactory Receptor. Both the primary signal and the amplified or multiple amplified signals can be detected so as to increase the dynamic range of binding interactions detected by the biosensor.

The biosensor can include one or more reporters. A heterologous gene encoding a reporter protein can be introduced into the host cell such that the host cell expresses the reporter, and the biosensor activates the reporter when an appropriate interaction occurs at the Olfactory Receptor of the biosensor. The host cells can be engineered to express a single reporter. Different host cells, each expressing a different reporter, can be used to enhance signal detection of the biosensor. The host cell can be engineered to express two or more reporter products, for example by using a single vector construct encoding two or more reporters. The reporter or reporters can provide a dynamic range of detection over at least 3, 4, 5, 6, 7, 8, 9, or 10 orders of magnitude, covering a range of detection at Olfactory Receptors in the range of from about $10^{-12}$ M to about 10 M.

The reporter or reporters can be one or more of a fluorescent reporter, a bioluminescent reporter, an enzyme, and an ion channel. Examples of fluorescent reporters include, for example, green fluorescent protein from *Aequorea victoria* or *Renilla reniformis*, and active variants thereof (e.g., blue fluorescent protein, yellow fluorescent protein, cyan fluorescent protein, etc.); fluorescent proteins from Hydroid jellyfishes, Copepod, Ctenophora, Anthrozoas, and Entacmaea quadricolor, and active variants thereof; and phycobiliproteins and active variants thereof. Other fluorescent reporters include, for example, small molecules such as CPSD (Disodium 3-(4-methoxyspiro {1,2-dioxetane-3,2'-(5'-chloro)tricyclo [$3.3.1.1^{3,7}$]decan}-4-yl) phenyl phosphate, ThermoFisher Catalog #T2141). Bioluminescent reporters include, for example, aequorin (and other $Ca^{+2}$ regulated photoproteins), luciferase based on luciferin substrate, luciferase based on Coelenterazine substrate (e.g., *Renilla, Gaussia,* and *Metridina*), and luciferase from Cypridina, and active variants thereof. The bioluminescent reporter can be, for example, North American firefly luciferase, Japanese firefly luciferase, Italian firefly luciferase, East European firefly luciferase, Pennsylvania firefly luciferase, Click beetle luciferase, railroad worm luciferase, *Renilla* luciferase, *Gaussia* luciferase, Cypridina luciferase, Metrida luciferase, OLuc, and red firefly luciferase, all of which are commercially available from ThermoFisher Scientific and/or Promega. Enzyme reporters include, for example, β-galactosidase, chloramphenicol acetyltransferase, horseradish peroxidase, alkaline phosphatase, acetylcholinesterase, and catalase. Ion channel reporters, include, for example, cAMP activated cation channels. The reporter or reporters may also include a Positron Emission Tomography (PET) reporter, a Single Photon Emission Computed Tomography (SPECT) reporter, a photoacoustic reporter, an X-ray reporter, and an ultrasound reporter.

Real time measurements can be made with the biosensors described herein. The reporter emits light or produces a molecule that can be detected with an optical sensor. Real time measurements can be obtained from the biosensor by recording the change in light emission over time as the biosensor interacts with a potential ligand. The real time measurements can be used to quantify the binding interaction by an absolute measurement or a relative measurement. In the absolute measurement, the real time signal is compared to a standard to determine the binding activity at the Olfactory Receptor. Known amounts of ligand for an Olfactory Receptor can be used to generate a standard binding curve for receptor occupancy versus reporter gene output. Binding of a test ligand can then be compared to the standard curve to quantify interaction of the test ligand at the Olfactory Receptor. In the relative measurement, the biosensor can include internal references that allow differences in interactions at an Olfactory Receptor to be compared. A reference G protein coupled receptor can be included in the host cell, and a known amount of the reference ligand is added to the reference receptor to act as a standard. The reference receptor can be coupled to a different reporter, e.g., a reporter polypeptide that provides a different optical signal from the Olfactory Receptor reporter. The reference and test receptors can be coupled to different fluorescent protein such as green fluorescent protein, GFP, and red fluorescent protein, RFP. The ratio of green fluorescence to red fluorescence could be compared for different test ligands at the same Olfactory Receptor, or to compare binding of the same test ligand to different Olfactory Receptors.

Real time data can be obtained from a biosensor with a non-optical reporter. The signal from a first reporter system can be amplified by a second reporter system so as to increase the signal from weak interactions at an Olfactory Receptor. The GTP/GDP ratio of the biosensor can be controlled to regulate the sensitivity of the G-protein coupled signal transduction from the receptor. The GTP/GDP ratio can be controlled to alter the dynamic range of the biosensor.

The product of the reporter gene can be detected by any appropriate detection method and apparatus, depending on the type of reporter product expressed from the reporter gene. By way of example, an exemplary reporter gene encodes a light producing protein (e.g., luciferase or eGFP), and this phenotype can be detected using optical imaging. In the descriptions herein, expression of a reporter is meant to include expression of the corresponding reporter gene resulting in expression of the encoded reporter or reporter molecule.

The polypeptides include polypeptides encoded by nucleic acids that hybridize under stringent hybridization conditions to nucleic acids encoding one of the polypeptides of SEQ ID NOS: 5-9 and 11-16, or encoding one of the human Olfactory Receptors from the 18 families of human olfactory receptors. The polypeptides also include polypeptides encoded by nucleic acids that hybridize under stringent hybridization conditions to nucleic acids encoding the polypeptide of SEQ ID NO: 5 or 6.

The polypeptides may have at least 70%, 80%, 90%, 95%, or 99% sequence identity to one of SEQ ID NOS: 5-9 and 11-16, or one of the human OR receptors from the 18 families of human olfactory receptors. The polypeptides may have at least 70%, 80%, 90%, 95%, or 99% sequence identity to one of SEQ ID NOS: 5-6.

The threshold of detection of human Olfactory Receptors in the biosensors can be from about 0.15 parts per billion to about 420,000 parts per billion or over a range of 6-7 orders of magnitude. The range of detection of human Olfactory Receptors in the biosensors described herein are from about $10^{-9}$ M to about $10^{-3}$ M or over a range of about 6 orders of magnitude. The range of detection can be over 3, 4, 5, 6, 7, 8, 9, or 10 orders of magnitude in the range of ligand from 10 M to $10^{-12}$ M.

The polypeptides can encompass fragments and variants of the polypeptides described herein. Thus, the term "fragment or variant polypeptide" further contemplates deletions, additions and substitutions to the sequence, so long as the polypeptide functions as described herein. The term "conservative variation" denotes the replacement of an amino acid residue by another biologically similar residue, or the replacement of a nucleotide in a nucleic acid sequence such that the encoded amino acid residue does not change or is changed to another structurally, chemically or otherwise functionally similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine, threonine, and tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

"Variant" polypeptides or nucleic acids encompass polypeptides or nucleic acids with substantially similar sequences. For polynucleotides, a variant comprises a deletion and/or addition of one or more nucleotides at one or more sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. Variants of a particular polynucleotide (i.e., the reference polynucleotide) can also be evaluated by comparison of the percent sequence identity between the polypeptide encoded by a variant polynucleotide and the polypeptide encoded by the reference polynucleotide. "Variant" protein is intended to mean a protein derived from the native protein by deletion or addition of one or more amino acids at one or more sites in the native protein and/or substitution of one or more amino acids at one or more sites in the native protein. Variant proteins are biologically active.

Homologs of polypeptides from other alleles are intended to be within the scope of the description. As used herein, the term "homologs" includes analogs and paralogs. The term "analogs" refers to two polynucleotides or polypeptides that have the same or similar function, but that have evolved separately in unrelated host organisms. The term "paralogs" refers to two polynucleotides or polypeptides that are related by duplication within a genome. Paralogs usually have different functions, but these functions may be related. Analogs and paralogs of a wild-type polypeptide can differ from the wild-type polypeptide by post-translational modifications, by amino acid sequence differences, or by both. In particular, homologs will generally exhibit at least 80-85%, 85-90%, 90-95%, or 95%, 96%, 97%, 98%, 99% sequence identity, with all or part of the wild-type polypeptide or polynucleotide sequences, and will exhibit a similar function. Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same genetic locus in those species. Any and all such nucleic acid variations and resulting amino acid polymorphisms or variations that are the result of natural allelic variation and that do not alter the functional activity of the gene of interest, are intended to be within the scope of the disclosure.

As used herein, the term "derivative" or "variant" refers to a polypeptide, or a nucleic acid encoding a polypeptide, that has one or more conservative amino acid variations or other minor modifications such that (1) the corresponding polypeptide has substantially equivalent function when compared to the wild type polypeptide or (2) an antibody raised against the polypeptide that is immunoreactive with the wild-type polypeptide. These variants or derivatives include polypeptides having minor modifications of the polypeptide primary amino acid sequences that may result in peptides which have substantially equivalent activity as compared to the unmodified counterpart polypeptide. Such modifications may be deliberate, as by site-directed mutagenesis, or may be spontaneous. The term "variant" further contemplates deletions, additions and substitutions to the sequence, so long as the polypeptide functions. The term "variant" also includes the modification of a polypeptide where the native signal peptide is replaced with a heterologous signal peptide to facilitate the expression or secretion of the polypeptide from a host species.

Polypeptides may include amino acid sequences for introducing a glycosylation site or other site for modification or derivatization of the polypeptide. The polypeptides described above may include the amino acid sequence N-X-S or N-X-T that can act as a glycosylation site. During glycosylation, an oligosaccharide chain is attached to asparagine (N) occurring in the tripeptide sequence N-X-S or N-X-T, where X can be any amino acid except Pro. This sequence is called a glycosylation sequence. This glycosylation site may be placed at the N-terminus, C-terminus, or within the internal sequence of the polypeptide.

Host Cells

Various eukaryotic cells can be used as the host cell. The host cell can be a fungal cell, animal cell, plant cell, or algae cell. In some embodiments, the eukaryotic cells are fungi cells, including, but not limited to, fungi of the genera *Aspergillus, Trichoderma, Saccharomyces, Chrysosporium, Klyuveromyces, Candida, Pichia, Debaromyces, Hansenula, Yarrowia, Zygosaccharomyces, Schizosaccharomyces, Penicillium*, or *Rhizopus*. The fungi cells can be *Saccharomyces cerevisiae, Pichia pastoris, Aspergillus niger, Aspergillus oryzae, Chrysosporium lucknowense*, or *Trichoderma reesei*.

The host cells can be animal cells. The host cells can be cells from a commercially valuable livestock. The animal cells can be mammalian cells, such as that of bovine, canine, feline, hamster, mouse, porcine, rabbit, rat, or sheep. The mammalian cells can be cells of primates, including but not limited to, monkeys, chimpanzees, gorillas, and humans. The mammalians cells can be mouse cells, as mice routinely function as a model for other mammals, most particularly for humans (see, e.g., Hanna, J. et al., "Treatment of sickle cell anemia mouse model with iPS cells generated from autologous skin," *Science* 318:1920-23, 2007; Holtzman, D. M. et al., "Expression of human apolipoprotein E reduces amyloid-β deposition in a mouse model of Alzheimer's disease," *J Clin Invest.* 103(6):R15-R21, 1999; Warren, R. S. et al., "Regulation by vascular endothelial growth factor of human colon cancer tumorigenesis in a mouse model of experimental liver metastasis," *J Clin Invest.* 95: 1789-1797, 1995; each publication incorporated herein by reference). Animal cells include, for example, fibroblasts, epithelial cells (e.g., renal, mammary, prostate, lung), keratinocytes, hepatocytes, adipocytes, endothelial cells, hematopoietic cells. The animal cells can be adult cells (e.g., terminally differentiated, dividing or non-dividing) or stem cells. Mammalian cell lines can be used as host cells. The cell lines can be derived from Chinese hamster cells, Human kidney cells, Monkey kidney cells, Human cervical cancer cells, or Mouse myeloma cells. These and other mammalian cell lines are well known in the art, for example, the mammalian cell lines publicly available from ThermoFisher Scientific, ATCC (American Type Culture Collection), and Charles River Laboratories International, Inc. The cell lines disclosed at the web-sites for ThermoFisher, ATCC, and Charles River Laboratories are incorporate by reference in their entirety for all purposes.

The eukaryotic cells can be plant cells. The plant cells can be cells of monocotyledonous or dicotyledonous plants, including, but not limited to, alfalfa, almonds, asparagus, avocado, banana, barley, bean, blackberry, brassicas, broccoli, cabbage, canola, carrot, cauliflower, celery, cherry, chicory, citrus, coffee, cotton, cucumber, eucalyptus, hemp, lettuce, lentil, maize, mango, melon, oat, papaya, pea, peanut, pineapple, plum, potato (including sweet potatoes), pumpkin, radish, rapeseed, raspberry, rice, rye, sorghum, soybean, spinach, strawberry, sugar beet, sugarcane, sunflower, tobacco, tomato, turnip, wheat, zucchini, and other fruiting vegetables (e.g. tomatoes, pepper, chili, eggplant, cucumber, squash etc.), other bulb vegetables (e.g., garlic, onion, leek etc.), other pome fruit (e.g. apples, pears etc.), other stone fruit (e.g., peach, nectarine, apricot, pears, plums etc.), *Arabidopsis*, woody plants such as coniferous and deciduous trees, an ornamental plant, a perennial grass, a forage crop, flowers, other vegetables, other fruits, other agricultural crops, herbs, grass, or perennial plant parts (e.g., bulbs; tubers; roots; crowns; stems; stolons; tillers; shoots; cuttings, including un-rooted cuttings, rooted cuttings, and callus cuttings or callus-generated plantlets; apical meristems etc.). The term "plants" refers to all physical parts of a plant, including seeds, seedlings, saplings, roots, tubers, stems, stalks, foliage and fruits.

The eukaryotic cells can be algal, including but not limited to algae of the genera *Chlorella, Chlamydomonas, Scenedesmus, Isochrysis, Dunaliella, Tetraselmis, Nannochloropsis*, or *Prototheca*.

Nucleic Acids

Nucleic acids may encode, at least in part, the individual peptides, polypeptides, and proteins described herein. The nucleic acids may be natural, synthetic or a combination thereof. The nucleic acids of may be RNA, mRNA, DNA, cDNA, or synthetic nucleic acids.

The nucleic acids also can include expression vectors, such as plasmids, or viral vectors, or linear vectors, or vectors that integrate into chromosomal DNA. Expression vectors can contain a nucleic acid sequence that enables the vector to replicate in one or more selected host cells. Such sequences are well known for a variety of cells. The origin of replication from the plasmid pBR322 is suitable for most Gram-negative bacteria. In eukaryotic host cells, e.g., mammalian cells, the expression vector can be integrated into the host cell chromosome and then replicate with the host chromosome. Similarly, vectors can be integrated into the chromosome of prokaryotic cells. The vector can be related to the autonomously replicating plasmids in yeast YRp, YEp, and YCp. All three are *S. cerevisiae/E. coli* shuttle vectors that typically carry a multiple cloning site (MCS) for the insertion of expression cassettes. The yeast epitope tagging vectors, pESC can be used. The pESC vectors are commercially available from Agilent Technologies.

Expression vectors also generally contain a selection gene, also termed a selectable marker. Selectable markers are well-known in the art for prokaryotic and eukaryotic cells, including host cells. Generally, the selection gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. An exemplary selection scheme can utilize a drug to arrest growth of a host cell. Those cells that are successfully transformed with a heterologous gene produce a protein conferring drug resistance and thus survive the selection regimen. Other selectable markers for use in bacterial or eukaryotic (including mammalian) systems are well-known in the art. Examples of yeast selection genes, include, URA3, TRP1, LEU2, HIS3, LYS2, ADE2, MET15, hphNT1, and natNT2. Da Silva et al., FEMS Yeast Research 12:197-214 (2012), which is incorporated by reference in its entirety for all purposes. These yeast selection genes can be used with appropriate auxotrophic yeast strains.

Inducible promoters are also contemplated for use herein. Examples of inducible promoters include, but are not limited to yeast promoters for GAL1, GAL7, and GAL10 (galactose-inducible) CUP1 (copper ion inducible), ADH2 (glucose repression), and mammalian promoters such as a metallothionein promoter, a glucocorticoid promoter, a progesterone promoter, a c-fos promoter, the T-REx system of ThermoFisher which places expression from the human cytomegalovirus immediate-early promoter under the control of tetracycline operator(s), and RheoSwitch promoters of Intrexon. Karzenowski, D. et al., BioTechiques 39:191-196 (2005); Dai, X. et al., Protein Expr. Purif 42:236-245 (2005); Palli, S. R. et al., Eur. J. Biochem. 270:1308-1515 (2003); Dhadialla, T. S. et al., Annual Rev. Entomol. 43:545-569 (1998); Kumar, M. B, et al., J. Biol. Chem. 279:27211-27218 (2004); Verhaegent, M. et al., Annal. Chem. 74:4378-4385 (2002); Katalam, A. K., et al., Molecular Therapy 13:S103 (2006); and Karzenowski, D. et al., Molecular Therapy 13:S194 (2006), Da Silva et al., FEMS Yeast Research 12:197-214 (2012); U.S. Pat. Nos. 8,895,306, 8,822,754, 8,748,125, 8,536,354, all of which are incorporated by reference in their entirety for all purposes.

Expression vectors typically have promoter elements, e.g., enhancers, to regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

The nucleic acid can be operably linked to another nucleic acid so as to be expressed under control of a suitable promoter. The nucleic acid can be also operably linked to, in order to attain efficient transcription of the nucleic acid, other regulatory elements that cooperate with a promoter or a transcription initiation site, for example, a nucleic acid comprising an enhancer sequence, a polyA site, or a terminator sequence. In addition to the nucleic acid, a gene that can be a marker for confirming expression of the nucleic acid (e.g. a drug resistance gene, a gene encoding a reporter enzyme, or a gene encoding a fluorescent protein) may be incorporated.

It may be desirable to modify the polypeptides described herein. One of skill will recognize many ways of generating alterations in a given nucleic acid construct to generate variant polypeptides Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques (see, e.g., Gillam and Smith, Gene 8:81-97, 1979; Roberts et al., *Nature* 328:731-734, 1987, which is incorporated by reference in its entirety for all purposes). The recombinant nucleic acids encoding the polypeptides can be modified to provide preferred codons which enhance translation of the nucleic acid in a selected organism.

The polynucleotides also include polynucleotides including nucleotide sequences that are substantially equivalent to the polynucleotides of the invention. Polynucleotides can have at least about 80%, more typically at least about 90%, and even more typically at least about 95%, sequence identity to a polynucleotide for an Olfactory Receptor or other protein described herein. Polynucleotides also include the complement of the polynucleotides including a nucleotide sequence that has at least about 80%, more typically at least about 90%, and even more typically at least about 95%, sequence identity to a polynucleotide encoding a polypeptide recited herein. The polynucleotide can be DNA (genomic, cDNA, amplified, or synthetic) or RNA. Methods and algorithms for obtaining such polynucleotides are well known to those of skill in the art and can include, for example, methods for determining hybridization conditions which can routinely isolate polynucleotides of the desired sequence identities.

Nucleic acids which encode protein analogs or variants (i.e., wherein one or more amino acids are designed to differ from the wild type polypeptide) may be produced using site directed mutagenesis or PCR amplification in which the primer(s) have the desired point mutations. For a detailed description of suitable mutagenesis techniques, see Sambrook et al., Molecular Cloning: A Laboratory Manual, Cold Spring Harbor Laboratory Press, Cold Spring Harbor, N.Y. (1989) and/or Current Protocols in Molecular Biology, Ausubel et al., eds, Green Publishers Inc. and Wiley and Sons, N.Y (1994), each of which is incorporated by reference in its entirety for all purposes. Chemical synthesis using methods well known in the art, such as that described by Engels et al., *Angew Chem Intl Ed.* 28:716-34, 1989 (which is incorporated by reference in its entirety for all purposes), may also be used to prepare such nucleic acids.

Amino acid "substitutions" for creating variants can be preferably the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

"Insertions" or "deletions" are typically in the range of about 1 to 5 amino acids. The variation allowed may be experimentally determined by systematically making insertions, deletions, or substitutions of amino acids in a polypeptide molecule using recombinant DNA techniques and assaying the resulting recombinant variants for activity.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, or degradation/turnover rate.

Alternatively, where alteration of function is desired, insertions, deletions or non-conservative alterations can be engineered to produce altered polypeptides or chimeric polypeptides. Such alterations can, for example, alter one or more of the biological functions or biochemical characteristics of the polypeptides. For example, such alterations may change polypeptide characteristics such as ligand-binding affinities or degradation/turnover rate. Further, such alterations can be selected so as to generate polypeptides that are better suited for expression, scale up and the like in the host cells chosen for expression.

Polynucleotides encoding the polypeptides described herein can be changed via site-directed mutagenesis. This method uses oligonucleotide sequences that encode the polynucleotide sequence of the desired amino acid variant, as well as a sufficient adjacent nucleotide on both sides of the changed amino acid to form a stable duplex on either side of the site of being changed. In general, the techniques of site-directed mutagenesis are well known to those of skill in the art, and this technique is exemplified by publications such as, Edelman et al., *DNA* 2:183 (1983). A versatile and efficient method for producing site-specific changes in a polynucleotide sequence is described in Zoller and Smith, *Nucleic Acids Res.* 10:6487-6500 (1982).

PCR may also be used to create amino acid sequence variants of the nucleic acids. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the target at the position specified by the primer. The product DNA fragments replace the corresponding region in the plasmid and this gives the desired amino acid variant.

A further technique for generating amino acid variants is the cassette mutagenesis technique described in Wells et al., Gene 34:315 (1985), and other mutagenesis techniques well known in the art, such as, for example, the techniques in Sambrook et al., supra, and Ausubel et al., supra.

Process for Making Host Cells with Biosensors

As described above, Olfactory Receptors, including ectopic Olfactory Receptors, can be genetically engineered for expression in a desired host cell. The Olfactory Receptors may be from a certain species, or maybe fusion or hybrid constructs. The N-terminal and C-terminal sequences of the Olfactory Receptor or fusion/hybrid localize the Olfactory Receptor or fusion/hybrid to the host cell membrane, and if appropriate to the outer membrane of a host cell. These Olfactory Receptor or fusion/hybrid gene constructs are placed into appropriate expression vectors for the host cell and then these expression constructs or expression vectors are placed inside a host cell.

The host cells can be genetically engineered to express human G protein subunits. The host cells also can be genetically engineered to express the human G protein subunits G$\alpha$, G$\beta$, and G$\gamma$. The genes encoding the human G$\alpha$, G$\beta$, and G$\gamma$ subunits can be placed under the control of appropriate control sequences (promoters, enhancers, translation start sequences, polyA sites, etc.) for the desired host cell, and these constructs for the human G$\alpha$, G$\beta$, and G$\gamma$ subunits are placed into the desired host cell. The human G protein also can be associated with adenylate cyclase. The gene for an appropriate adenylate cyclase can be placed under the control of appropriate control sequences for the desired host cell, and this construct is placed into the desired host cell.

In the processes described herein, a eukaryotic host cell as describe above can be used. A fungal cell can be used. The fungal cell can be from the *Aspergillus, Trichoderma, Saccharomyces, Chrysosporium, Klyuveromyces, Candida, Pichia, Debaromyces, Hansenula, Yarrowia, Zygosaccharomyces, Schizosaccharomyces, Penicillium,* or *Rhizopus* genera. The fungal cell can be a *Saccharomyces cerevisiae*. A eukaryotic cell derived from a mammal, for example, a human cell, or a cell derived from a non-human mammal such as a monkey, a mouse, a rat, a pig, a horse, or a dog can be used. The cell used in the processes described herein is not particularly limited, and any cell can be used.

The nucleic acid encoding the biosensor can be introduced to the host cell by transfection (e.g., Gorman, et al. Proc. Natl. Acad. Sci. 79.22 (1982): 6777-6781, which is incorporated by reference in its entirety for all purposes), transduction (e.g., Cepko and Pear (2001) Current Protocols in Molecular Biology unit 9.9; DOI: 10.1002/ 0471142727.mb0909s36, which is incorporated by reference in its entirety for all purposes), calcium phosphate transformation (e.g., Kingston, Chen and Okayama (2001) Current Protocols in Molecular Biology Appendix 1C; DOI: 10.1002/0471142301.nsa01cs01, which is incorporated by reference in its entirety for all purposes), cell-penetrating peptides (e.g., Copolovici, Langel, Eriste, and Langel (2014) ACS Nano 2014 8 (3), 1972-1994; DOI: 10.1021/ nn4057269, which is incorporated by reference in its entirety for all purposes), electroporation (e.g Potter (2001) Current Protocols in Molecular Biology unit 10.15; DOI: 10.1002/0471142735.im1015s03 and Kim et al (2014) Genome 1012-19. doi:10.1101/gr.171322.113, Kim et al. 2014 describe the Amaza Nucleofector, an optimized electroporation system, both of these references are incorporated by reference in their entirety for all purposes), microinjection (e.g., McNeil (2001) Current Protocols in Cell Biology unit 20.1; DOI: 10.1002/0471143030.cb2001s18, which is incorporated by reference in its entirety for all purposes), liposome or cell fusion (e.g., Hawley-Nelson and Ciccarone (2001) Current Protocols in Neuroscience Appendix 1F; DOI: 10.1002/0471142301.nsa01fs10, which is incorporated by reference in its entirety for all purposes), mechanical manipulation (e.g. Sharon et al. (2013) PNAS 2013 110(6); DOI: 10.1073/pnas.1218705110, which is incorporated by reference in its entirety for all purposes) or other well-known technique for delivery of nucleic acids to eukaryotic cells. Once introduced, the nucleic acid can be transiently expressed episomally, or can be integrated into the genome of the eukaryotic cell using well known techniques such as recombination (e.g., Lisby and Rothstein (2015) Cold Spring Harb Perspect Biol. March 2; 7(3). pii: a016535. doi: 10.1101/cshperspect.a016535, which is incorporated by reference in its entirety for all purposes), or non-homologous integration (e.g., Deyle and Russell (2009) Curr Opin Mol Ther. 2009 August; 11(4):442-7, which is incorporated by reference in its entirety for all purposes). The efficiency of homologous and non-homologous recombination can be facilitated by genome editing technologies that introduce targeted double-stranded breaks (DSB). Examples of DSB-generating technologies are CRISPR/ Cas9, TALEN, Zinc-Finger Nuclease, or equivalent systems (e.g., Cong et al Science 339.6121 (2013): 819-823, Li et al. Nucl. Acids Res (2011): gkr188, Gaj et al. Trends in Biotechnology 31.7 (2013): 397-405, all of which are incorporated by reference in their entirety for all purposes), transposons such as Sleeping Beauty (e.g., Singh et al (2014) Immunol Rev. 2014 January; 257(1):181-90. doi: 10.1111/ imr.12137, which is incorporated by reference in its entirety for all purposes), targeted recombination using, for example, FLP recombinase (e.g., O'Gorman, Fox and Wahl Science (1991) 15:251(4999):1351-1355, which is incorporated by reference in its entirety for all purposes), CRE-LOX (e.g., Sauer and Henderson PNAS (1988): 85; 5166-5170), or equivalent systems, or other techniques known in the art for integrating the nucleic acid into the eukaryotic cell genome.

The nucleic acid(s) encoding the Gα, Gβ, Gγ, adenylate cyclase, and the Olfactory Receptor can be integrated into the eukaryotic host cell chromosome at a genomic safe harbor site, such as, for example, the CCR5, AAVS1, human ROSA26, or PSIP1 loci for human cells. (Sadelain et al., Nature Rev. 12:51-58 (2012); Fadel et al., J. Virol. 88(17): 9704-9717 (2014); Ye et al., PNAS 111(26):9591-9596 (2014), all of which are incorporated by reference in their entirety for all purposes.) Safe harbor sites for yeast cells, e.g., Saccharomyces cerevisiae, include, for example, yeast Ty δ sequences. The host cell can be a human cell and the integration of the nucleic acid(s) encoding the Gα, Gβ, Gγ, adenylate cyclase, and the Olfactory Receptor at the CCR5 and/or PSIP1 locus is done using a gene editing system, such as, for example, CRISPR, TALEN, or Zinc-Finger nuclease systems. The eukaryotic cell can be a Saccharomyces cerevisiae cell and a CRISPR system is used to integrate the Gα, Gβ, Gγ, adenylate cyclase, and the Olfactory Receptor at Ty δ locus. Integration of the nucleic acid at safe harbor loci using the CRISPR system also can delete a portion, or all, of the safe harbor loci. Cas9 in the eukaryotic cell may be derived from a plasmid encoding Cas9, an exogenous mRNA encoding Cas9, or recombinant Cas9 polypeptide alone or in a ribonucleoprotein complex. (Kim et al (2014) Genome 1012-19. doi:10.1101/gr.171322.113.; Wang et al (2013) Cell 153 (4). Elsevier Inc.: 910-18. doi:10.1016/ j.cell.2013.04.025, both of which are incorporated by reference in their entirety for all purposes.)

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

Ligands for Ectopic Olfactory Receptors

Ligands for ectopic Olfactory Receptors can be any known or novel compound, and examples include nucleic acids, carbohydrates, lipids, proteins, peptides, low molecular weight organic compounds (small molecules), compound libraries prepared using the technology of combinatorial chemistry, random peptide libraries prepared by solid phase synthesis or phage display method or natural products derived from microorganisms, animals and plants, and marine organism. Ligands for ectopic Olfactory Receptors include, for example, antibodies (including full length antibodies, antibody fragments, single chain antibodies, etc.), large and small polypeptides, and small molecules.

Antibodies can be obtained following immunization of a suitable animal with one of the ectopic Olfactory Receptors described above. Methods for immunizing an animal with a membrane protein such as an ectopic Olfactory Receptor include those described in, for example, Satofuka et al, Biochem. Biophys. Res. Comm., 450:99-104 (2014), Hansen et al., Scientific Reports 6:article number 21925 (2016), doi:10.1038/srep21925, Tamura et al., J. Biomed. Biotechnol. Vol. 2009, Article ID 673098, dx.doi.org/10.1155/2009/ 673098, Banik et al., Drug Discovery Development 12:14- 17 (2009), which are incorporated by reference in their entirety for all purposes. Antibodies specific for the ectopic Olfactory Receptor can be obtained from an immunized animal, for example, by screening hybridomas from made from the immune cells of the immunized animal. Such hybridomas can include those made from a mouse that is transgenic for the human (or other) immunoglobulin loci (e.g., Jakobavits, 1998, Adv Drug Deliv Rev. 31:33-42, which is hereby incorporated by reference in its entirety). Antibodies can also be obtained for an ectopic Olfactory Receptor by using the ectopic Olfactory Receptor with in vitro methods utilizing recombinant libraries of antibody fragments displayed on and encoded in filamentous bacteriophage (e.g., McCafferty et al., 1990, Nature 348:552-554, which is hereby incorporated by reference in its entirety), yeast cells (e.g., Boder and Wittrup, 1997, Nat Biotechnol 15:553-557, which is hereby incorporated by reference in its entirety), and ribosomes (e.g., Hanes and Pluckthun, 1997, Proc Natl Acad Sci USA 94:4937-4942, which is hereby incorporated by reference in its entirety) are panned against immobilized antigen. Once isolated, antibodies can be engineered for use in a particular organism. The organism can be a human, canine, or a commercially valuable livestock, such as, for example, pigs, horses, dogs, cats, chickens, or other birds. Such engineering of the antibody includes, for example, humanization, humaneering, chimerization, or isolating human (or other organism) antibodies using any of the repertoire technologies or monoclonal technologies known in the art.

Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (N.C.), or are readily producible. Additionally, natural and synthetically produced libraries and compounds are readily modified through conventional chemical, physical, and biochemical means (Blondelle et al., (1996) Tib Tech 14:60, which is incorporated by reference in its entirety for all purposes).

Methods for preparing libraries of molecules are well known and many libraries are commercially available. Such libraries include peptide libraries, randomized oligonucleotide libraries, synthetic organic combinatorial libraries, and the like. Degenerate peptide libraries can be readily prepared in solution, in immobilized form as bacterial flagella peptide display libraries or as phage display libraries. Peptide ligands can be selected from combinatorial libraries of peptides containing at least one amino acid. Libraries can be synthesized of peptoids and non-peptide synthetic moieties. Such libraries can further be synthesized which contain non-peptide synthetic moieties, which are less subject to enzymatic degradation compared to their naturally-occurring counterparts. Libraries are also meant to include for example but are not limited to peptide-on-plasmid libraries, polysome libraries, aptamer libraries, synthetic peptide libraries, synthetic small molecule libraries and chemical libraries. The libraries can also comprise cyclic carbon or heterocyclic structure and/or aromatic or polyaromatic structures substituted with one or more of the above-identified functional groups.

Small molecule combinatorial libraries may also be generated. A combinatorial library of small organic compounds is a collection of closely related analogs that differ from each other in one or more points of diversity and are synthesized by organic techniques using multi-step processes. Combinatorial libraries include a vast number of small organic compounds. One type of combinatorial library is prepared by means of parallel synthesis methods to produce a compound array. A compound array can be a collection of compounds identifiable by their spatial addresses in Cartesian coordinates and arranged such that each compound has a common molecular core and one or more variable structural diversity elements. The compounds in such a compound array are produced in parallel in separate reaction vessels, with each compound identified and tracked by its spatial address. Examples of parallel synthesis mixtures and parallel synthesis methods are provided in U.S. Ser. No. 08/177,497, filed Jan. 5, 1994 and its corresponding PCT published patent application WO95/18972, published Jul. 13, 1995 and U.S. Pat. No. 5,712,171 granted Jan. 27, 1998 and its corresponding PCT published patent application WO96/22529, which are incorporated by reference in their entirety for all purposes.

Examples of chemically synthesized libraries are described in Fodor et al., (1991) Science 251:767-773; Houghten et al., (1991) Nature 354:84-86; Lam et al., (1991) Nature 354:82-84; Medynski, (1994) BioTechnology 12:709-710; Gallop et al., (1994) J. Medicinal Chemistry 37(9):1233-1251; Ohlmeyer et al., (1993) Proc. Natl. Acad. Sci. USA 90:10922-10926; Erb et al., (1994) Proc. Natl. Acad. Sci. USA 91:11422-11426; Houghten et al., (1992) Biotechniques 13:412; Jayawickreme et al., (1994) Proc. Natl. Acad. Sci. USA 91:1614-1618; Salmon et al., (1993) Proc. Natl. Acad. Sci. USA 90:11708-11712; PCT Publication No. WO 93/20242, dated Oct. 14, 1993; and Brenner et al., (1992) Proc. Natl. Acad. Sci. USA 89:5381-5383, all of which are incorporated by reference in their entirety for all purposes.

Nucleic acids encoding the components of a biosensor (e.g., an ectopic Olfactory Receptor, G-proteins, and adenylate cyclase and/or other reporter) can be placed in a suitable host cell (e.g., *Saccharomyces cerevisiae*) and the host cells with the biosensor can be used to identify ligands for the ectopic Olfactory Receptor. These host cells can be lysed and membrane fraction can be obtained that include the ectopic Olfactory Receptor, G-proteins, and adenylate cyclase (and/or other reporter). These membrane fractions can be used as the biosensor for detection of ligands. For example, antibodies obtained from immunizations with the ectopic Olfactory Receptor, or obtained from panning against the ectopic Olfactory Receptor can be tested against the biosensors to look for agonists and antagonists. The biosensors of the ectopic Olfactory Receptors can also be used to find polypeptide or small molecule agonists and antagonists. Potential agonists and antagonists can be obtained by panning libraries of peptides or small molecules against the ectopic Olfactory Receptor. Examples of panning include adhering ectopic Olfactory Receptors to a substrate and then exposing those adhered ectopic Olfactory Receptors to libraries of antibodies, polypeptides, or small molecules to identify members of the library that bind to the ectopic Olfactory Receptor. The members that bind to the ectopic Olfactory Receptor are then screened against biosensors made with the ectopic Olfactory Receptor to find agonists and antagonists. Agonists may be full agonists, partial agonists, inverse agonists (binds to a receptor and produces the opposite pharmacological response from an agonist), or neutral agonists (blocks the effect of an agonist or inverse agonist at a receptor). Ligands can also be allosteric modulators including positive allosteric modulators or negative allosteric modulators.

The degree of interaction that a ligand has with an ectopic Olfactory Receptor can be characterized and quantified using the biosensors. Ligands can be tested against a repertoire of biosensors for some or all of the ectopic Olfactory Receptors found on a tissue or cell. The interaction of the ligand with the repertoire of ectopic Olfactory Receptors can make an aromagraph for the ligand(s). The biosensors made with the ectopic Olfactory Receptors can be used to deconstruct the aromagraph of natural ligands that interact with the ectopic Olfactory Receptors of a tissue or cell to identify which ectopic Olfactory Receptors are stimulated and the degree of stimulation (the aromagraph). Such aromagraphs can be used to make a mixture or ligands (e.g., artificial ligands) that mimic the aromagraph of the natural ligands for the ectopic Olfactory Receptors. These aromagraphs can also be used to deconstruct components that contribute to the aromagraph by using different mixtures of natural ligands (or different derivatives of a ligand) and identifying changes in the aromagraph. For example, a composition can be deconstructed by removing components and identifying changes to the aromagraph.

Pharmaceutical Compositions

Pharmaceutical compositions may comprise a ligand for an ectopic Olfactory Receptor in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Pharmaceutical compositions may be administered in a manner appropriate to the disease or condition to be treated (or prevented). The quantity and frequency of administration will be determined by such factors as the condition of the patient, and the type and severity of the patient's disease, although appropriate dosages may be determined by clinical trials.

Suitable pharmaceutically acceptable excipients are well known to a person skilled in the art. Examples of the pharmaceutically acceptable excipients include phosphate buffered saline (e.g. 0.01 M phosphate, 0.138 M NaCl, 0.0027 M KCl, pH 7.4), an aqueous solution containing a mineral acid salt such as a hydrochloride, a hydrobromide, a phosphate, or a sulfate, saline, a solution of glycol or ethanol, and a salt of an organic acid such as an acetate, a propionate, a malonate or a benzoate. An adjuvant such as a wetting agent or an emulsifier, and a pH buffering agent can also be used. The pharmaceutically acceptable excipients described in Remington's Pharmaceutical Sciences (Mack Pub. Co., N.J. 1991) (which is incorporated herein by reference in its entirety for all purposes) can be appropriately used. The ligand compositions can be formulated into a known form suitable for parenteral administration, for example, injection or infusion (e.g., any ligand can be administered in this fashion, including antibodies, other polypeptides, and small molecules). Alternatively, the ligand can be formulated for oral administration, nasal or other mucosal tissue administration, or administration as a suppository (e.g., for small molecules). The ligand compositions may comprise formulation additives such as a suspending agent, a preservative, a stabilizer and/or a dispersant, and a preservation agent for extending a validity term during storage.

Pharmaceutical compositions comprising a ligand for an ectopic Olfactory Receptor may be manufactured by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers, diluents, excipients, or auxiliaries, which facilitate processing of ligands or crystalline forms thereof and one or more pharmaceutically acceptable vehicles into formulations that can be used pharmaceutically. Proper formulation is dependent upon the route of administration chosen. Pharmaceutical compositions may take the form of solutions, suspensions, emulsion, tablets, pills, pellets, capsules, capsules containing liquids, powders, sustained-release formulations, suppositories, emulsions, aerosols, sprays, suspensions, or any other form suitable for administration to a patient.

A composition comprising a ligand for an ectopic Olfactory Receptor as an active ingredient can be administered for treatment of, for example, wound healing, bone and cartilage growth to repair bones, nerve regeneration and repair, organ repair, corneal repair, and angiogenesis. The ligand compositions can be used in the treatment of melanoma, Parkinson's disease, Alzheimer's, used in contraception or fertility, used to stimulate hair growth, etc.

The administration of the subject compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, intranasally, intraarterially, into an afferent lymph vessel, by intravenous (i.v.) injection, or intraperitoneally. Alternatively, the ligand compositions may be incorporated into pharmaceutical compositions to be administered by other appropriate routes of administration including intranasal, epidural, oral, sublingual, intracerebral, intravaginal, transdermal, rectal, inhalation, or topical.

When "an effective amount," "a therapeutically effective amount," or "a tumor-inhibiting effective amount" is indicated, the precise amount of the ligand compositions to be administered can be determined by a physician with consideration of individual differences in age, weight, tumor size, extent of infection or metastasis, and condition of the patient (subject). A pharmaceutical composition comprising a ligand described herein may be administered at a dosage of from about 10 g/kg to about 50 mg/kg, from about 100 μg/kg to about 50 mg/kg, from about 1 mg/kg to about 50 mg/kg, and in certain embodiments, from about 5 mg/kg to about 25 mg/kg, including all integer values within those ranges. Ligands for ectopic Olfactory Receptors may be administered at a dose over time from about 1 mg to about 5 g per day, from about 10 mg to about 4 g per day, or from about 20 mg to about 2 g per day, including all integer values within those ranges. A ligand composition may also be administered multiple times at these dosages.

Uses of Ectopic Olfactory Receptors

Ectopic Olfactory Receptors can be used in a variety of therapeutic, diagnostic and nontherapeutic applications. For example, ectopic Olfactory Receptors can be stimulated by agonists to induce skin growth for wound healing, bone and cartilage growth to repair bones, nerve regeneration and repair, organ repair, corneal repair, angiogenesis, etc. Ectopic Olfactory Receptors can also be used to inhibit angiogenesis in cancer, used in the treatment of melanoma, Parkinson's disease, Alzheimer's, used in contraception or fertility, used to stimulate hair growth, etc. Ectopic Olfactory Receptors can be used to stimulate proper embryological growth, maturation, differentiation, development, and/or tissue organization (e.g., in cases of prenatal or postnatal improper development such as spina bifida, cleft lip/palate, etc.).

Ligands for the ectopic Olfactory Receptor (e.g., the ectopic Olfactory Receptors described above) can be used to bind the ectopic Olfactory Receptor in an animal, for example, a mammal including humans or mice. When the ectopic Olfactory Receptor binds the ligand (e.g., an antibody) this can stimulate the receptor and activate the cell displaying the ectopic Olfactory Receptor. This activation of the cell can induce the cell to proliferate, differentiate, secrete factors, migrate, etc. Alternatively, the ligand can block the ectopic Olfactory Receptor and prevent other ligands from binding to the ectopic Olfactory Receptor, or the ligand may act allosterically on the ectopic Olfactory Receptor.

The ectopic Olfactory Receptor, OR2AT4 has been found in keratinocytes and stimulation of this ectopic Olfactory Receptor with agonists caused proliferation, migration and regeneration of cell layers. Agonists such as sandalore, brahmanol, antibodies, and other agonists of OR2AT4 can be applied to wounds to stimulate the growth of keratinocytes during wound healing. For example, a wound dressing (e.g., a band aid) could have a hydrogel layer in which the agonist of OR2AT4 is dispersed for extended release of the agonist to stimulate wound healing. Suitable hydrogels for would dressing include, for example, crosslinked 2-hydroxyethyl methacrylate, commercial hydrogels such as, for example, Geliperm®, Curasol® and Tegagel®, collagen, chitin derivatives, chitosan, alginic acid, sodium alginate, starch, starch derivatives, dextran, glucan, gelatin, poly-N-acetyl glucosamine, hyaluronic acid, hyaluronan, bacterial cellulose, keratin, silk, polyurethane, poly(methyl methacrylate), proplasts, alloplastics, poly(N-vinylpyrolidone), PEG, poly(N-isopropylacrylamide), clay nanocomposite membranes, metal oxide composite membranes, carbon-based material composite membranes.

The ectopic Olfactory Receptors OR51E2, OR51E1, OR2J3, and VN1R1 are expressed in neural tissue and cells. The ectopic Olfactory Receptor OR51E2 is found in a variety of neural tissue including, for example, the substantia nigra where it plays a role in melanogenesis. Ligands for OR51E2 include, for example, antibodies or molecules that have a carbonyl group conjugated to a butadiene system such as isoprenoid 3-ionone (violet scent), α-4,6-androstaiene-17-ol-3-one, 6-dehydrotestosterone, and 1,4,6-androstadiene-3,17-dione. Stimulation of melanogenesis can be neuroprotective and useful in the treatment of neurodegenerative diseases such as Parkinson's Disease and Alzheimer's. The ectopic Olfactory Receptor VN1R1 is found in a variety of neural tissue including, for example, the limbic areas (e.g., amygdala and hippocampus). Ligands for VN1R1 include, for example, antibodies and the common floral odor phenylethyl alcohol and hedione. Stimulation of VN1R1 receptors in neural tissue can induce the secretion of sex hormones which are known to have neuroprotective properties against Parkinson's Disease and other neurodegenerative diseases.

Biosensors can be used to detect and diagnose disease. Many diseases are associated with odors or smells that can be used to diagnose the disease. For example, certain lung, liver, kidney and digestive diseases can be detected from a patient's breath, diabetes, schizophrenia, Parkinson's, and certain infectious diseases (tuberculosis and typhoid) can be detected by a patient's odor, and some cancers can be detected by the olfactory repertoire of canines. Odors, scent, and/or smell associated with a patient's skin, sweat, hair, saliva, and other body secretions (e.g., ear wax) can be associated with disease diagnosis. Biosensor with the ectopic Olfactory Receptor can be used to create aromagraphs of patient's with diseases that can be detected by odor, scent, and/or smell. These aromagraphs can be based on a human repertoire of Olfactory Receptors or a repertoire of ectopic Olfactory Receptors. The aromagraph is based on a canine repertoire of Olfactory Receptors. The aromagraph can be based on a mouse or rat repertoire of Olfactory Receptors. The aromagraph can be based on a mammalian repertoire of Olfactory Receptors. Patients can then be diagnosed for disease by taking odor, breath or other samples and screening them to see whether the aromagraph for a certain disease is detected.

Biosensors can also be used to identify sets of ectopic Olfactory Receptors that are associated with disease. Panels of ligands for the disease specific ectopic Olfactory Receptor(s) can be made and can be used to monitor a disease by observing the changes in a patient's response at the ectopic Olfactory Receptor(s) associated with the disease. For example, a poor sense of smell is one of the early warning signs of Alzheimer's. The degradation of the sense of smell is associated with both a loss of the ability of the brain to sense some Olfactory Receptors and the loss of Olfactory Receptor memory (association of a smell with the stimulation of certain Olfactory Receptors). The loss of Olfactory Receptor response and Olfactory Receptor memory can be used as an early warning sign for Alzheimer's, and can also be used to monitor response to anti-Alzheimer's treatment, as the loss of smell is reversible in some cases. Patients at risk for Alzheimer's can be tested for loss of smell at disease associated Olfactory Receptors, and for Olfactory Receptor memory. Patients who reach a certain age can be screened for loss of smell at disease associated Olfactory Receptors and for Olfactory Receptor memory. Panels of odorants can be used to monitor a patient's sense of smell at the disease associated Olfactory Receptors or ectopic Olfactory Receptors. The panel of odorants can have different interactions at the disease associated Olfactory Receptors from strong to weak interactions. The biosensor can be used to identify disease associated Olfactory Receptors and to identify ligands that can be used to diagnose early Alzheimer's.

The biosensors can also be used in drug discovery. The biosensors can be used to design the taste, smell, odor, scent, and/or aroma of a drug and/or pharmaceutical composition. The biosensors can be used to identify and mask a taste, smell, odor, scent, and/or aroma associated with a drug and/or pharmaceutical composition. The taste, smell, odor, scent, and/or aroma which is masked can produce a negative response in certain subjects. The taste, smell, odor, scent, and/or aroma which is masked can produce a positive or addictive response in certain subjects (addiction inhibition). The biosensors can be used to design abuse-deterrent formulations. The adversant formulations can be used for opioid drugs including, for example, hydrocodone (Vicodin), oxycodone (OxyContin, Percocet, Roxicodone, Oxecta), morphine (Kadian, Avinza), codeine, buprenorphine (Buprenex, Butrans), butorphanol (Stadol), hydromorphone (Dilaudid, Hydrostat, Exalgo), levorphanol (Levo-Dromoran), meperidine (Demerol), methadone (Dolophine, Methadose), nalbuphine (Nubain), oxymorphone (Numorphan), pentazocine (Talwin), propoxyphene (Cotanal-65, Darvon), fentanyl (Sublimaze, Actiq, Durogesic, Fentora, Matrifen, Hadid, Onsolis, Instanyl, Abstral, Lazanda), tramadol (Ultram), and tapentadol (Nucynta). An adversant can be included in the formulation that produces a taste, smell, odor, scent, and/or aroma that produces an avoidance behavior or other strongly negative reaction by subjects. The adversant can be comprised of two or more components that when sensed together produce the negative reaction, but when sensed individually do not induce the negative reaction. The two or more components can be engineered in the abuse deterrent formulation to be released at different times, but when the formulation is crushed or extracted to abuse the drug, this releases both components to form the adversant. The adversant formed when the two components combine can become a gas at room temperature, or become a gas after the components mix and the drug formulation is heated.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

EXAMPLES

Example 1: Making a Biosensor in a Yeast Cell

The N-terminal 55 amino acids of the human OR6A2 receptor are fused to the N-terminal region of the human OR1A1 receptor in place of the N-terminal 55 amino acids of OR1A1 to give a biosensor Olfactory Receptor with the sequence:

```
                                          (SEQ ID NO: 11)
MEWRNHSGRV SEFVLLGFPA PAPLQVLLFA LLLLAYVLVL

TENTLIIMAI RNHSTHNPMY FLLANLSLVD IFFSSVTIPK

MLANHLLGSK SISFGGCLTQ MYFMIALGNT DSYILAAMAY

DRAVAISRPL HYTTIMSPRS CIWLIAGSWV IGNANALPHT

LLTASLSFCG NQEVANFYCD ITPLLKLSCS DIHFHVKMMY

LGVGIFSVPL LCIIVSYIRV FSTVFQVPST KGVLKAFSTC

GSHLTVVSLY YGTVMGTYFR PLTNYSLKDA VITVMYTAVT

PMLNPFIYSL RNRDMKAALR KLFNKRISS
```

A nucleic acid encoding this Olfactory Receptor is engineered into a yeast cell that has been previously engineered to express the human G protein subunits Gα, Gβ, and Gγ, and adenylate cyclase. Yeast were engineered with constructs that placed the human Gα, Gβ, and Gγ subunits:

```
                                          (SEQ ID NO: 12)
MGCLGGNSKTTEDQGVDEKERREANKKIEKQLQKERLAYKATHRLLLLGA

GESGKSTIVKQMRILHVNGFNPEEKKQKILDIRKNVKDAIVTIVSAMSTI

IPPVPLANPENQFRSDYIKSIAPITDFEYSQEFFDHVKKLWDDEGVKACF

ERSNEYQLIDCAQYFLERIDSVSLVDYTPTDQDLLRCRVLTSGIFETRFQ

VDKVNFHMFDVGGQRDERRKWIQCFNDVTAIIYVAACSSYNMVIREDNNT

NRLRESLDLFESIWNNRWLRTISIILFLNKQDMLAEKVLAGKSKIEDYFP

EYANYTVPEDATPDAGEDPKVTRAKFFIRDLFLRISTATGDGKHYCYPHF

TCAVDTENIRRVFNDCRDIIQRMHLKQYELL
```

```
                                          (SEQ ID NO: 13)
MSELEQLRQEAEQLRNQIRDARKACGDSTLTQITAGLDPVGRIQMRTRRT

LRGHLAKIYAMHWGTDSRLLVSASQDGKLIIWDSYTTNKVHAIPLRSSWV

MTCAYAPSGNFVACGGLDNICSIYSLKTREGNVRVSRELPGHTGYLSCCR

FLDDNQIITSSGDTTCALWDIETGQQTVGFAGHSGDVMSLSLAPDGRTFV

SGACDASIKLWDVRDSMCRQTFIGHESDINAVAFFPNGYAFTTGSDDATC

RLFDLRADQELLMYSHDNIICGITSVAFSRSGRLLLAGYDDFNCNIWDAM

KGDRAGVLAGHDNRVSCLGVTDDGMAVATGSWDSFLKIWN
```

```
                                          (SEQ ID NO: 14)
MSGSSSVAAMKKVVQQLRLEAGLNRVKVSQAAADLKQFCLQNAQHDPLLT

GVSSSTNPFRPQKVCSFL
``` under the control of either the yeast GAL1 or GAL10 promoter. The yeast strain was also engineered to express human adenylate cyclase (human adenylate cyclase type 5, NP 001186571.1):

```
                                          (SEQ ID NO: 15)
MPRNQGFSEPEYSAEYSAEYSVSLPSDPDRGVGRTHEISVRNSGSCLCLP

RFMRLTFVPESLENLYQTYFKRQRHETLLVLVVFAALFDCYVVVMCAVVF

SSDKLASLAVAGIGLVLDIILFVLCKKGLLPDRVTRRVLPYVLWLLITAQ

IFSYLGLNFARAHAASDTVGWQVFFVFSFFITLPLSLSPIVIISVVSCVV

HTLVLGVTVAQQQQEELKGMQLLREILANVFLYLCAIAVGIMSYYMADRK

HRKAFLEARQSLEVKMNLEEQSQQQENLMLSILPKHVADEMLKDMKKDES

QKDQQQFNTMYMYRHENVSILFADIVGFTQLSSACSAQELVKLLNELFAR

FDKLAAKYHQLRIKILGDCYYCICGLPDYREDHAVCSILMGLAMVEAISY

VREKTKTGVDMRVGVHTGTVLGGVLGQKRWQYDVWSTDVTVANKMEAGGI

PGRVHISQSTMDCLKGEFDVEPGDGGSRCDYLEEKGIETYLIIASKPEVK

KTATQNGLNGSALPNGAPASSKSSSPALIETKEPNGSAHSSGSTSEKPEE

QDAQADNPSFPNPRRRLRLQDLADRVVDASEDEHELNQLLNEALLERESA

QVVKKRNTFLLSMRFMDPEMETRYSVEKEKQSGAAFSCSCVVLLCTALVE

ILIDPWLMTNYVTFMVGEILLLILTICSLAAIFPRAFPKKLVAFSTWIDR

TRWARNTWAMLAIFILVMANVVDMLSCLQYYTGPSNATAGMETEGSCLEN

PKYYNYVAVLSLIATIMLVQVSHMVKLTLMLLVAGAVATINLYAWRPVFD

EYDHKRFREHDLPMVALEQMQGFNPGLNGTDRLPLVPSKYSMTVMVFLMM

LSFYYFSRHVEKLARTLFLWKIEVHDQKERVYEMRRWNEALVTNMLPEHV

ARHFLGSKKRDEELYSQTYDEIGVMFASLPNFADFYTEESINNGGIECLR

FLNEIISDFDSLLDNPKFRVITKIKTIGSTYMAASGVTPDVNTNGFASSN

KEDKSERERWQHLADLADFALAMKDTLTNINNQSFNNFMLRIGMNKGGVL

AGVIGARKPHYDIWGNTVNVASRMESTGVMGNIQVVEETQVILREYGFRF

VRRGPIFVKGKGELLTFFLKGRDKLATFPNGPSVTLPHQVVDNS
```

Or human adenylate cyclase 3 (UniProtKB: O60266):

(SEQ ID NO: 16)
MPRNQGFSEPEYSAEYSAEYSVSLPSDPDRGVGRTHEISVRNSGSCLCLP

RFMRLTFVPESLENLYQTYFKRQRHETLLVLVVFAALFDCYVVVMCAVVF

SSDKLASLAVAGIGLVLDIILFVLCKKGLLPDRVTRRVLPYVLWLLITAQ

IFSYLGLNFARAHAASDTVGWQVFFVFSFFITLPLSLSPIVIISVVSCVV

HTLVLGVTVAQQQQEELKGMQLLREILANVFLYLCAIAVGIMSYYMADRK

HRKAFLEARQSLEVKMNLEEQSQQQENLMLSILPKHVADEMLKDMKKDES

QKDQQQFNTMYMYRHENVSILFADIVGFTQLSSACSAQELVKLLNELFAR

FDKLAAKYHQLRIKILGDCYYCIGLPDYREDHAVCSILMGLAMVEAISY

VREKTKTGVDMRVGVHTGTVLGGVLGQKRWQYDVWSTDVTVANKMEAGGI

PGRVHISQSTMDCLKGEFDVEPGDGGSRCDYLEEKGIETYLIIASKPEVK

KTATQNGLNGSALPNGAPASSKSSSPALIETKEPNGSAHSSGSTSEKPEE

QDAQADNPSFPNPRRRLRLQDLADRVVDASEDEHELNQLLNEALLERESA

QVVKKRNTFLLSMRFMDPEMETRYSVEKEKQSGAAFSCSCVVLLCTALVE

ILIDPWLMTNYVTFMVGEILLLILTICSLAAIFPRAFPKKLVAFSTWIDR

TRWARNTWAMLAIFILVMANVVDMLSCLQYYTGPSNATAGMETEGSCLEN

PKYYNYVAVLSLIATIMLVQVSHMVKLTLMLLVAGAVATINLYAWRPVFD

EYDHKRFREHDLPMVALEQMQGFNPGLNGTDRLPLVPSKYSMTVMVFLMM

LSFYYFSRHVEKLARTLFLWKIEVHDQKERVYEMRRWNEALVTNMLPEHV

ARHFLGSKKRDEELYSQTYDEIGVMFASLPNFADFYTEESINNGGIECLR

FLNEIISDFDSLLDNPKFRVITKIKTIGSTYMAASGVTPDVNTNGFASSN

KEDKSERERWQHLADLADFALAMKDTLTNINNQSFNNFMLRIGMNKGGVL

AGVIGARKPHYDIWGNTVNVASRMESTGVNIGNIQVVEETQVILREYGFR

FVRRGPIFVKGKGELLTFFLKGRDKLATFPNGPSVTLPHQVVDNS under the control of either the yeast GAL I or GAL10 promoters.

Biosensors with yeast cells expressing the hybrid olfactory receptor, the human Gα, Gβ, and Gγ subunits, and human adenylate cyclase are tested for expression of the components and for signal transduction by the hybrid OR.

Example 2: Using Real Time Detection to Quantitate Ligand Binding at a Repertoire of Olfactory Receptors A plurality of biosensors as described in Example 1, are used for human Olfactory Receptors from OR Family OR7. The Yeast cells with the OR7 family Olfactory Receptors are also genetically modified to include a recombinant GFP gene expressed by a control region activated by cAMP. Thus, when the biosensor is activated by an odorant, the biosensor will produce GFP and activity can be monitored by fluorescence.

Olfactory Receptors in the OR7 family are receptors for mammalian pheromones such as those related to androstenone. A panel of odorants is screened against a panel of androstenone related molecules, including, androstadienol (5,16-androstadien-3β-ol), androstadienone (androsta-4,16,-dien-3-one), androstanol (5α-androst-16-en-3α-ol), and estratetraenol (estra-1,3,5(10),16-tetraen-3-ol).

Yeast cells expressing different members of the OR7 family of Olfactory Receptors are placed into separate wells or containers, interrogated with individual odorants from the panel, and fluorescence readings are made at time points 0, 10 seconds, 20 seconds, 30 seconds, 1 minute, 2 minutes, 3 minutes, 4 minutes, 5 minutes, 10 minutes, 20 minutes, 30 minutes, 40 minutes, 50 minutes, and 1 hour.

Example 3: Making a Biosensor with Human Olfactory Receptor OR1A1

The full length human olfactory receptor OR1A1 was used to make the expression plasmids NIXp218 and NIXp354. In both NIXp218 and NIXp354, the nucleic acid encoding OR1A1 is under the control of a GAL1-10 promoter. A general plasmid map for the OR constructs is shown in FIG. 1. In NIXp354, OR1A1 is fused at its N-terminal end with a FLAG tag (SEQ ID NO:17), and at its C-terminal end with the coding sequence for red fluorescent protein (RFP).

Plasmid NIXp354 or NIXp218 was placed in a haploid Saccharomyces cerevisiae (MATa strain). Expression of OR1A1 from NIXp354 is monitored using the FLAG tag to measure expression (using an immunoassay) and cellular localization of the OR1A1 is monitored by fluorescence from the RFP. Function of the biosensor is assessed by mating the Saccharomyces cerevisiae strain with NIXp218 to the complementary Saccharomyces cerevisiae strain (MATα) which is modified with the human G protein subunits Gα, Gβ, and Gγ, and adenylate cyclase. Mating together these two yeast strains brings the OR1A1 receptor into functional association with human G protein subunits Gα, Gβ, and Gγ, and adenylate cyclase. Function of the OR1A1 receptor can be assessed by a cAMP assay following stimulation of the OR1A1 receptor.

Example 4: Making a Biosensor with Human Olfactory Receptor OR2J2

The full length human olfactory receptor OR2J2 was used to make the expression plasmids NIXp219 and NIXp352. In both NIXp219 and NIXp352, the nucleic acid encoding OR2J2 is under the control of a GAL1-10 promoter. A plasmid map for the OR constructs is shown in FIG. 1. In NIXp352, OR2J2 is fused at its N-terminal end with a FLAG tag (SEQ ID NO:17), and at its C-terminal end with the coding sequence for red fluorescent protein (RFP).

Plasmid NIXp352 or NIXp219 was placed in haploid Saccharomyces cerevisiae (MATa strain). Expression of OR2J2 from NIXp352 is monitored using the FLAG tag to measure expression (using an immunoassay) and cellular localization of the OR2J2 is monitored by fluorescence from the RFP. Function of the biosensor is assessed by mating the Saccharomyces cerevisiae strain with NIXp219 to the complementary Saccharomyces cerevisiae strain (MATα) which is modified with the human G protein subunits Gα, Gβ, and Gγ, and adenylate cyclase. Mating together these two yeast strains brings the OR2J2 receptor into functional association with human G protein subunits Gα, Gβ, and Gγ, and adenylate cyclase. Function of the OR2J2 receptor can be assessed by a cAMP assay following stimulation of the OR2J2 receptor.

Example 5: Making a Biosensor with Human Olfactory Receptor OR2W1

The full length human olfactory receptor OR2W1 was used to make expression plasmids NIXp220 and NIXp351.

In both NIXp220 and NIXp351, the nucleic acid encoding OR2W1 is under the control of a GAL1-10 promoter. A plasmid map for the OR constructs is shown in FIG. 1. In NIXp351, OR2W1 is fused at its N-terminal end with a FLAG tag (SEQ ID NO:17), and at its C-terminal end with the coding sequence for red fluorescent protein (RFP).

Plasmid NIXp351 or NIXp220 was placed in haploid *Saccharomyces cerevisiae* (MATa strain). Expression of OR2W1 from NIXp351 is monitored using the FLAG tag to measure expression (using an immunoassay) and cellular localization of the OR2W1 is monitored by fluorescence from the RFP. Function of the biosensor is assessed by mating the *Saccharomyces cerevisiae* strain with NIXp220 to the complementary *Saccharomyces cerevisiae* strain (MATα) which is modified with the human G protein subunits Gα, Gβ, and Gγ, and adenylate cyclase. Mating together these two yeast strains brings the OR2W1 receptor into functional association with human G protein subunits Gα, Gβ, and Gγ, and adenylate cyclase. Function of the OR2W1 receptor can be assessed by a cAMP assay following stimulation of the OR2W1 receptor.

Example 6: Making a Biosensor with Human Olfactory Receptor OR5P3

The full length human olfactory receptor OR5P3 was used to make the expression plasmids NIXp217 and NIXp353. In both NIXp217 and NIXp353, the nucleic acid encoding OR5P3 is under the control of a GAL1-10 promoter. A plasmid map for the OR constructs is shown in FIG. 1. In NIXp353, OR5P3 is fused at its N-terminal end with a FLAG tag (SEQ ID NO:17), and at its C-terminal end with the coding sequence for red fluorescent protein (RFP).

Plasmid NIXp353 or NIXp217 was placed in haploid *Saccharomyces cerevisiae* (MATa strain). Expression of OR5P3 from NIXp353 is monitored using the FLAG tag to measure expression (using an immunoassay) and cellular localization of the OR5P3 is monitored by fluorescence from the RFP. Function of the biosensor is assessed by mating the *Saccharomyces cerevisiae* strain with NIXp217 to complementary *Saccharomyces cerevisiae* strain (MATα) which is modified with the human G protein subunits Gα, Gβ, and Gγ, and adenylate cyclase. Mating together these two yeast strains brings the OR5P3 receptor into functional association with human G protein subunits Gα, Gβ, and Gγ, and adenylate cyclase. Function of the OR5P3 receptor can be assessed by a cAMP assay following stimulation of the OR5P3 receptor.

Example 7: Making a Biosensor with Human Olfactory Receptor OR6A2

The full length human olfactory receptor OR6A2 was used to make the expression plasmid NIXp239. In NIXp239 the nucleic acid encoding OR6A2 is under the control of a GAL1-10 promoter. A plasmid map for the OR construct is shown in FIG. 1.

Plasmid NIXp239 was placed in haploid *Saccharomyces cerevisiae* (MATa strain). Function of the biosensor is assessed by mating the *Saccharomyces cerevisiae* strain with NIXp239 to the complementary *Saccharomyces cerevisiae* strain (MATα) which is modified with the human G protein subunits Gα, Gβ, and Gγ, and adenylate cyclase. Mating together these two yeast strains brings the OR6A2 receptor into functional association with human G protein subunits Gα, Gβ, and Gγ, and adenylate cyclase. Function of the OR6A2 receptor can be assessed by a cAMP assay following stimulation of the OR6A2 receptor.

Example 8: Making a Cell Extract with a Biosensor

In this example the yeast cells with biosensors made from OR1A1, OR2J2, OR2W1, OR5P3, and OR6A2 from Examples 3-7 are used. Yeast cells with the Olfactory Receptor, G-proteins and adenylate cyclase are lysed with glass beads in a blender. Cell debris is removed by centrifuging the lysate at 600×g. The remaining lysate is centrifuged in an ultracentrifuge (104,300×g) to obtain the membrane fraction with the Olfactory Receptor, G-proteins and adenylate cyclase. The membrane fraction is resuspended and placed into a multiwell plate for detection of odorants.

Example 9: Making a Biosensor with Human Olfactory Receptor OR51E2

The full length human olfactory receptor OR51E2 is used to make ane expression plasmid. In the expression plasmid, the nucleic acid encoding OR51E2 is under the control of a GAL1-10 promoter. A plasmid map for the OR construct is shown in FIG. 1.

The expression plasmid for OR51E2 is placed in haploid *Saccharomyces cerevisiae* (MATa strain). Function of the biosensor is assessed by mating this *Saccharomyces cerevisiae* strain with the complementary *Saccharomyces cerevisiae* strain (MATα) which is modified with the human G protein subunits Gα, Gβ, and Gγ, and adenylate cyclase. Mating together these two yeast strains brings the OR51E2 receptor into functional association with human G protein subunits Gα, Gβ, and Gγ, and adenylate cyclase. Function of the OR51E2 receptor can be assessed by a cAMP assay following stimulation of the OR51E2 receptor.

Example 10: Making a Biosensor with Human Olfactory Receptor OR2AT4

The full length human olfactory receptor OR2AT4 is used to make ane expression plasmid. In the expression plasmid, the nucleic acid encoding OR2AT4 is under the control of a GAL1-10 promoter. A plasmid map for the OR construct is shown in FIG. 1.

The expression plasmid for OR2AT4 is placed in haploid *Saccharomyces cerevisiae* (MATa strain). Function of the biosensor is assessed by mating this *Saccharomyces cerevisiae* strain with the complementary *Saccharomyces cerevisiae* strain (MATα) which is modified with the human G protein subunits Gα, Gβ, and Gγ, and adenylate cyclase. Mating together these two yeast strains brings the OR2AT4 receptor into functional association with human G protein subunits Gα, Gβ, and Gγ, and adenylate cyclase. Function of the OR2AT4 receptor can be assessed by a cAMP assay following stimulation of the OR2AT4 receptor.

Example 11: Making a Biosensor with Human Olfactory Receptor OR2J3

The full length human olfactory receptor OR2J3 is used to make ane expression plasmid. In the expression plasmid, the nucleic acid encoding OR2J3 is under the control of a GAL1-10 promoter. A plasmid map for the OR construct is shown in FIG. 1.

The expression plasmid for OR2J3 is placed in haploid *Saccharomyces cerevisiae* (MATa strain). Function of the biosensor is assessed by mating this *Saccharomyces cerevi-* siae strain with the complementary *Saccharomyces cerevisiae* strain (MATα) which is modified with the human G protein subunits Gα, Gβ, and Gγ, and adenylate cyclase. Mating together these two yeast strains brings the OR2J3 receptor into functional association with human G protein subunits Gα, Gβ, and Gγ, and adenylate cyclase. Function of the OR2J3 receptor can be assessed by a cAMP assay following stimulation of the OR2J3 receptor.

Example 12: Making a Biosensor with Human Olfactory Receptor OR51E1

The full length human olfactory receptor OR51E1 is used to make an expression plasmid. In the expression plasmid, the nucleic acid encoding OR51E1 is under the control of a GAL1-10 promoter. A plasmid map for the OR construct is shown in FIG. 1.

The expression plasmid for OR51E1 is placed in haploid *Saccharomyces cerevisiae* (MATa strain). Function of the biosensor is assessed by mating this *Saccharomyces cerevisiae* strain with the complementary *Saccharomyces cerevisiae* strain (MATα) which is modified with the human G protein subunits Gα, Gβ, and Gγ, and adenylate cyclase. Mating together these two yeast strains brings the OR51E1 receptor into functional association with human G protein subunits Gα, Gβ, and Gγ, and adenylate cyclase. Function of the OR51E1 receptor can be assessed by a cAMP assay following stimulation of the OR51E1 receptor.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

Those skilled in the art will recognize, or be able to ascertain using no more than routine experimentation, many equivalents to the specific embodiments of the invention described herein. Such equivalents are intended to be encompassed by the following claims.

We claim:

1. A method for detecting an odorant, comprising the steps of: providing a repertoire of biosensors, wherein each biosensor comprises an ectopic Olfactory Receptor, a G protein subunit Gα, a G protein subunit Gβ, and a G protein subunit Gγ, and a reporter, wherein binding of the odorant to the ectopic Olfactory Receptor sends a signal through the G protein subunits resulting in a signal from the reporter; adding the odorant to the repertoire of biosensors; detecting a change in the reporter signal; and making a first Aromagraph from the reporter signals.

2. The method of claim 1, further comprising the step of comparing the first Aromagraph for the odorant to an Aromagraph for a known odorant.

3. The method of claim 1, further comprising the step of comparing the first Aromagraph for the odorant to a library of Aromagraphs for a library of odorants.

4. The method of claim 3, further comprising the step of finding an odorant that has an Aromagraph that matches the first Aromagraph.

5. The method of claim 1, further comprising the steps of comparing the Aromagraph to a standard curve of Aromagraphs for the odorant; and determining the concentration of the odorant.

6. The method of claim 1, wherein the biosensor is in an *Aspergillus*, a *Trichoderma*, a *Saccharomyces*, a *Chrysosporium*, a *Klyuveromyces*, a *Candida*, a *Pichia*, a *Debaromyces*, a *Hansenula*, a *Yarrowia*, a *Zygosaccharomyces*, a *Schizosaccharomyces*, a *Penicillium*, or a *Rhizopus*.

7. The method of claim 1, wherein the biosensor is in a membrane fraction of a host cell.

8. The method of claim 7, wherein the host cell is an *Aspergillus*, a *Trichoderma*, a *Saccharomyces*, a *Chrysosporium*, a *Klyuveromyces*, a *Candida*, a *Pichia*, a *Debaromyces*, a *Hansenula*, a *Yarrowia*, a *Zygosaccharomyces*, a *Schizosaccharomyces*, a *Penicillium*, or a *Rhizopus*.

9. The method of claim 7, further comprising the step of quantifying the binding of the odorant to the repertoire of biosensors.

10. The method of claim 9, wherein the step of quantifying comprises quantifying the binding at the ectopic Olfactory Receptors of the repertoire of biosensors.

11. The method of claim 7, wherein the reporter is an optical reporter.

12. The method of claim 11, further comprising the step of quantifying the binding of the odorant to the repertoire of biosensors in real time by measuring changes in the optical reporter over time.

13. The method of claim 12, further comprising the step of quantifying the binding of the odorant to a single biosensor in real time by measuring a change in the optical reporter over time.

14. The method of claim 1, wherein the ectopic Olfactory Receptors are expressed on a skin cell.

15. The method of claim 1, wherein the ectopic Olfactory Receptors are expressed on a brain cell.

16. The method of claim 1, wherein the ectopic Olfactory Receptors are expressed on a reproductive cell.

17. The method of claim 1, wherein the ectopic Olfactory Receptors are expressed on a white blood cell.

18. The method of claim 14, wherein the ectopic Olfactory Receptors includes an OR2AT4.

19. The method of claim 15, wherein the ectopic Olfactory Receptors includes an OR51E2, an OR51E1, or both.

* * * * *

```
                          SEQUENCE LISTING

<160> NUMBER OF SEQ ID NOS: 17

<210> SEQ ID NO 1
<211> LENGTH: 10
<212> TYPE: PRT
<213> ORGANISM: Artificial Sequence
<220> FEATURE:
<223> OTHER INFORMATION: Olfactory Receptor motiff

<400> SEQUENCE: 1

Met Ala Tyr Asp Arg Tyr Val Ala Ile Cys
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Olfactory Receptor motiff

<400> SEQUENCE: 2

Leu His Thr Pro Met Tyr
1               5

<210> SEQ ID NO 3
<211> LENGTH: 7
<212> TYPE: PRT
<213> ORGANISM: Artificial Sequence
<220> FEATURE:
<223> OTHER INFORMATION: Olfactory Receptor motiff

<400> SEQUENCE: 3

Phe Ser Thr Cys Ser Ser His
1               5

<210> SEQ ID NO 4
<211> LENGTH: 6
<212> TYPE: PRT
<213> ORGANISM: Artificial Sequence
<220> FEATURE:
<223> OTHER INFORMATION: olfactory Receptor motiff

<400> SEQUENCE: 4

Pro Met Leu Asn Pro Phe
1               5
```

<210> SEQ ID NO 5
<211> LENGTH: 309
<212> TYPE: PRT
<213> ORGANISM: Homo sapiens

<400> SEQUENCE: 5

Met Arg Glu Asn Asn Gln Ser Ser Thr Leu Glu Phe Ile Leu Leu Gly
1               5                   10                  15

Val Thr Gly Gln Gln Gln Gln Glu Asp Phe Phe Tyr Ile Leu Phe Leu
            20                  25                  30

Phe Ile Tyr Pro Ile Thr Leu Ile Gly Asn Leu Leu Ile Val Leu Ala
        35                  40                  45

Ile Cys Ser Asp Val Arg Leu His Asn Pro Met Tyr Phe Leu Leu Ala
    50                  55                  60

Asn Leu Ser Leu Val Asp Ile Phe Phe Ser Ser Val Thr Ile Pro Lys
65                  70                  75                  80

Met Leu Ala Asn His Leu Leu Gly Ser Lys Ser Ile Ser Phe Gly Gly
                85                  90                  95

Cys Leu Thr Gln Met Tyr Phe Met Ile Ala Leu Gly Asn Thr Asp Ser
            100                 105                 110

Tyr Ile Leu Ala Ala Met Ala Tyr Asp Arg Ala Val Ala Ile Ser Arg
        115                 120                 125

Pro Leu His Tyr Thr Thr Ile Met Ser Pro Arg Ser Cys Ile Trp Leu
    130                 135                 140

Ile Ala Gly Ser Trp Val Ile Gly Asn Ala Asn Ala Leu Pro His Thr
145                 150                 155                 160

Leu Leu Thr Ala Ser Leu Ser Phe Cys Gly Asn Gln Glu Val Ala Asn
                165                 170                 175

Phe Tyr Cys Asp Ile Thr Pro Leu Leu Lys Leu Ser Cys Ser Asp Ile
            180                 185                 190

His Phe His Val Lys Met Met Tyr Leu Gly Val Gly Ile Phe Ser Val
        195                 200                 205

Pro Leu Leu Cys Ile Ile Val Ser Tyr Ile Arg Val Phe Ser Thr Val
    210                 215                 220

Phe Gln Val Pro Ser Thr Lys Gly Val Leu Lys Ala Phe Ser Thr Cys
225                 230                 235                 240

Gly Ser His Leu Thr Val Val Ser Leu Tyr Tyr Gly Thr Val Met Gly
                245                 250                 255

Thr Tyr Phe Arg Pro Leu Thr Asn Tyr Ser Leu Lys Asp Ala Val Ile
            260                 265                 270

Thr Val Met Tyr Thr Ala Val Thr Pro Met Leu Asn Pro Phe Ile Tyr
        275                 280                 285

Ser Leu Arg Asn Arg Asp Met Lys Ala Ala Leu Arg Lys Leu Phe Asn
    290                 295                 300

Lys Arg Ile Ser Ser
305

<210> SEQ ID NO 6
<211> LENGTH: 327
<212> TYPE: PRT
<213> ORGANISM: Homo sapiens

<400> SEQUENCE: 6

Met Glu Trp Arg Asn His Ser Gly Arg Val Ser Glu Phe Val Leu Leu
1               5                   10                  15

```
Gly Phe Pro Ala Pro Ala Pro Leu Gln Val Leu Leu Phe Ala Leu Leu
            20                  25                  30

Leu Leu Ala Tyr Val Leu Val Leu Thr Glu Asn Thr Leu Ile Ile Met
        35                  40                  45

Ala Ile Arg Asn His Ser Thr Leu His Lys Pro Met Tyr Phe Phe Leu
50                  55                  60

Ala Asn Met Ser Phe Leu Glu Ile Trp Tyr Val Thr Val Thr Ile Pro
65                  70                  75                  80

Lys Met Leu Ala Gly Phe Val Gly Ser Lys Gln Asp His Gly Gln Leu
                85                  90                  95

Ile Ser Phe Glu Gly Cys Met Thr Gln Leu Tyr Phe Phe Leu Gly Leu
            100                 105                 110

Gly Cys Thr Glu Cys Val Leu Leu Ala Val Met Ala Tyr Asp Arg Tyr
        115                 120                 125

Met Ala Ile Cys Tyr Pro Leu His Tyr Pro Val Ile Val Ser Gly Arg
130                 135                 140

Leu Cys Val Gln Met Ala Ala Gly Ser Trp Ala Gly Gly Phe Gly Ile
145                 150                 155                 160

Ser Met Val Lys Val Phe Leu Ile Ser Gly Leu Ser Tyr Cys Gly Pro
                165                 170                 175

Asn Ile Ile Asn His Phe Phe Cys Asp Val Ser Pro Leu Leu Asn Leu
            180                 185                 190

Ser Cys Thr Asp Met Ser Thr Ala Glu Leu Thr Asp Phe Ile Leu Ala
        195                 200                 205

Ile Phe Ile Leu Leu Gly Pro Leu Ser Val Thr Gly Ala Ser Tyr Val
210                 215                 220

Ala Ile Thr Gly Ala Val Met His Ile Pro Ser Ala Ala Gly Arg Tyr
225                 230                 235                 240

Lys Ala Phe Ser Thr Cys Ala Ser His Leu Thr Val Val Ile Ile Phe
                245                 250                 255

Tyr Ala Ala Ser Ile Phe Ile Tyr Ala Arg Pro Lys Ala Leu Ser Ala
            260                 265                 270

Phe Asp Thr Asn Lys Leu Val Ser Val Leu Tyr Ala Val Ile Val Pro
        275                 280                 285

Leu Leu Asn Pro Ile Ile Tyr Cys Leu Arg Asn Gln Glu Val Lys Arg
290                 295                 300

Ala Leu Cys Cys Thr Leu His Leu Tyr Gln His Gln Asp Pro Asp Pro
305                 310                 315                 320

Lys Lys Ala Ser Arg Asn Val
                325

<210> SEQ ID NO 7
<211> LENGTH: 312
<212> TYPE: PRT
<213> ORGANISM: Homo sapiens

<400> SEQUENCE: 7

Met Met Ile Lys Lys Asn Ala Ser Ser Glu Asp Phe Ile Leu Leu
1               5                   10                  15

Gly Phe Ser Asn Trp Pro Gln Leu Glu Val Val Leu Phe Val Val Ile
            20                  25                  30

Leu Ile Phe Tyr Leu Met Thr Leu Thr Gly Asn Leu Phe Ile Ile Ile
        35                  40                  45

Leu Ser Tyr Val Asp Ser His Leu His Thr Pro Met Tyr Phe Phe Leu
```

Ser Asn Leu Ser Phe Leu Asp Leu Cys Tyr Thr Thr Ser Ser Ile Pro
65                  70                  75                  80

Gln Leu Leu Val Asn Leu Arg Gly Pro Glu Lys Thr Ile Ser Tyr Ala
            85                  90                  95

Gly Cys Met Val Gln Leu Tyr Phe Val Leu Ala Leu Gly Ile Thr Glu
            100                 105                 110

Cys Val Leu Leu Val Val Met Ser Tyr Asp Arg Tyr Val Ala Val Cys
            115                 120                 125

Arg Pro Leu His Tyr Thr Val Leu Met His Pro Arg Phe Cys His Leu
130                 135                 140

Leu Val Ala Ala Ser Trp Val Ile Gly Phe Thr Ile Ser Ala Leu His
145                 150                 155                 160

Ser Ser Phe Thr Phe Trp Val Pro Leu Cys Gly His Arg Leu Val Asp
            165                 170                 175

His Phe Phe Cys Glu Val Pro Ala Leu Leu Arg Leu Ser Cys Val Asp
            180                 185                 190

Thr His Ala Asn Glu Leu Thr Leu Met Val Met Ser Ser Ile Phe Val
            195                 200                 205

Leu Ile Pro Leu Ile Leu Ile Leu Thr Thr Tyr Gly Ala Ile Ala Arg
210                 215                 220

Ala Val Leu Ser Met Gln Ser Thr Thr Gly Leu Gln Lys Val Phe Arg
225                 230                 235                 240

Thr Cys Gly Ala His Leu Met Val Val Ser Leu Phe Phe Ile Pro Val
            245                 250                 255

Met Cys Met Tyr Leu Gln Pro Pro Ser Glu Asn Ser Pro Asp Gln Gly
            260                 265                 270

Lys Phe Ile Ala Leu Phe Tyr Thr Val Val Thr Pro Ser Leu Asn Pro
            275                 280                 285

Leu Ile Tyr Thr Leu Arg Asn Lys His Val Lys Gly Ala Ala Lys Arg
290                 295                 300

Leu Leu Gly Trp Glu Trp Gly Lys
305                 310

<210> SEQ ID NO 8
<211> LENGTH: 320
<212> TYPE: PRT
<213> ORGANISM: Homo sapiens

<400> SEQUENCE: 8

Met Asp Gln Ser Asn Tyr Ser Ser Leu His Gly Phe Ile Leu Leu Gly
1               5                   10                  15

Phe Ser Asn His Pro Lys Met Glu Met Ile Leu Ser Gly Val Val Ala
            20                  25                  30

Ile Phe Tyr Leu Ile Thr Leu Val Gly Asn Thr Ala Ile Ile Leu Ala
            35                  40                  45

Ser Leu Leu Asp Ser Gln Leu His Thr Pro Met Tyr Phe Phe Leu Arg
            50                  55                  60

Asn Leu Ser Phe Leu Asp Leu Cys Phe Thr Thr Ser Ile Ile Pro Gln
65                  70                  75                  80

Met Leu Val Asn Leu Trp Gly Pro Asp Lys Thr Ile Ser Tyr Val Gly
            85                  90                  95

Cys Ile Ile Gln Leu Tyr Val Tyr Met Trp Leu Gly Ser Val Glu Cys
            100                 105                 110

```
Leu Leu Leu Ala Val Met Ser Tyr Asp Arg Phe Thr Ala Ile Cys Lys
            115                 120                 125

Pro Leu His Tyr Phe Val Val Met Asn Pro His Leu Cys Leu Lys Met
130                 135                 140

Ile Ile Met Ile Trp Ser Ile Ser Leu Ala Asn Ser Val Val Leu Cys
145                 150                 155                 160

Thr Leu Thr Leu Asn Leu Pro Thr Cys Gly Asn Asn Ile Leu Asp His
                165                 170                 175

Phe Leu Cys Glu Leu Pro Ala Leu Val Lys Ile Ala Cys Val Asp Thr
            180                 185                 190

Thr Thr Val Glu Met Ser Val Phe Ala Leu Gly Ile Ile Ile Val Leu
        195                 200                 205

Thr Pro Leu Ile Leu Ile Leu Ile Ser Tyr Gly Tyr Ile Ala Lys Ala
210                 215                 220

Val Leu Arg Thr Lys Ser Lys Ala Ser Gln Arg Lys Ala Met Asn Thr
225                 230                 235                 240

Cys Gly Ser His Leu Thr Val Val Ser Met Phe Tyr Gly Thr Ile Ile
                245                 250                 255

Tyr Met Tyr Leu Gln Pro Gly Asn Arg Ala Ser Lys Asp Gln Gly Lys
            260                 265                 270

Phe Leu Thr Leu Phe Tyr Thr Val Ile Thr Pro Ser Leu Asn Pro Leu
        275                 280                 285

Ile Tyr Thr Leu Arg Asn Lys Asp Met Lys Asp Ala Leu Lys Lys Leu
290                 295                 300

Met Arg Phe His His Lys Ser Thr Lys Ile Lys Arg Asn Cys Lys Ser
305                 310                 315                 320

<210> SEQ ID NO 9
<211> LENGTH: 311
<212> TYPE: PRT
<213> ORGANISM: Homo sapiens

<400> SEQUENCE: 9

Met Gly Thr Gly Asn Asp Thr Thr Val Val Glu Phe Thr Leu Leu Gly
1               5                   10                  15

Leu Ser Glu Asp Thr Thr Val Cys Ala Ile Leu Phe Leu Val Phe Leu
                20                  25                  30

Gly Ile Tyr Val Val Thr Leu Met Gly Asn Ile Ser Ile Ile Val Leu
            35                  40                  45

Ile Arg Arg Ser His His Leu His Thr Pro Met Tyr Ile Phe Leu Cys
50                  55                  60

His Leu Ala Phe Val Asp Ile Gly Tyr Ser Ser Ser Val Thr Pro Val
65                  70                  75                  80

Met Leu Met Ser Phe Leu Arg Lys Glu Thr Ser Leu Pro Val Ala Gly
                85                  90                  95

Cys Val Ala Gln Leu Cys Ser Val Val Thr Phe Gly Thr Ala Glu Cys
            100                 105                 110

Phe Leu Leu Ala Ala Met Ala Tyr Asp Arg Tyr Val Ala Ile Cys Ser
        115                 120                 125

Pro Leu Leu Tyr Ser Thr Cys Met Ser Pro Gly Val Cys Ile Ile Leu
130                 135                 140

Val Gly Met Ser Tyr Leu Gly Gly Cys Val Asn Ala Trp Thr Phe Ile
145                 150                 155                 160

Gly Cys Leu Leu Arg Leu Ser Phe Cys Gly Pro Asn Lys Val Asn His
                165                 170                 175
```

```
Phe Phe Cys Asp Tyr Ser Pro Leu Leu Lys Leu Ala Cys Ser His Asp
            180                 185                 190

Phe Thr Phe Glu Ile Ile Pro Ala Ile Ser Ser Gly Ser Ile Ile Val
        195                 200                 205

Ala Thr Val Cys Val Ile Ala Ile Ser Tyr Ile Tyr Ile Leu Ile Thr
    210                 215                 220

Ile Leu Lys Met His Ser Thr Lys Gly Arg His Lys Ala Phe Ser Thr
225                 230                 235                 240

Cys Thr Ser His Leu Thr Ala Val Thr Leu Phe Tyr Gly Thr Ile Thr
                245                 250                 255

Phe Ile Tyr Val Met Pro Lys Ser Ser Tyr Ser Thr Asp Gln Asn Lys
            260                 265                 270

Val Val Ser Val Phe Tyr Thr Val Val Ile Pro Met Leu Asn Pro Leu
        275                 280                 285

Ile Tyr Ser Leu Arg Asn Lys Glu Ile Lys Gly Ala Leu Lys Arg Glu
    290                 295                 300

Leu Arg Ile Lys Ile Phe Ser
305                 310

<210> SEQ ID NO 10
<211> LENGTH: 100
<212> TYPE: PRT
<213> ORGANISM: Artificial Sequence
<220> FEATURE:
<223> OTHER INFORMATION: N-terminal Sequence of rat R17 Olfactory
      Receptor

<400> SEQUENCE: 10

Met Glu Arg Arg Asn His Ser Gly Arg Val Ser Glu Phe Val Leu Leu
1               5                   10                  15

Gly Phe Pro Ala Pro Ala Pro Leu Arg Val Leu Leu Phe Phe Leu Ser
            20                  25                  30

Leu Leu Ala Tyr Val Leu Val Leu Thr Glu Asn Met Leu Ile Ile Ile
        35                  40                  45

Ala Ile Arg Asn His Pro Thr Leu His Lys Pro Met Tyr Phe Phe Leu
    50                  55                  60

Ala Asn Met Ser Phe Leu Glu Ile Trp Tyr Val Thr Val Thr Ile Pro
65                  70                  75                  80

Lys Met Leu Ala Gly Phe Ile Gly Ser Lys Glu Asn His Gly Gln Leu
                85                  90                  95

Ile Ser Phe Glu
            100

<210> SEQ ID NO 11
<211> LENGTH: 309
<212> TYPE: PRT
<213> ORGANISM: Artificial Sequence
<220> FEATURE:
<223> OTHER INFORMATION: Fusion of OR6A2 and OR1A1

<400> SEQUENCE: 11

Met Glu Trp Arg Asn His Ser Gly Arg Val Ser Glu Phe Val Leu Leu
1               5                   10                  15

Gly Phe Pro Ala Pro Ala Pro Leu Gln Val Leu Leu Phe Ala Leu Leu
            20                  25                  30

Leu Leu Ala Tyr Val Leu Val Leu Thr Glu Asn Thr Leu Ile Ile Met
        35                  40                  45
```

Ala Ile Arg Asn His Ser Thr His Asn Pro Met Tyr Phe Leu Leu Ala
 50                  55                  60

Asn Leu Ser Leu Val Asp Ile Phe Phe Ser Val Thr Ile Pro Lys
 65                  70                  75                  80

Met Leu Ala Asn His Leu Leu Gly Ser Lys Ser Ile Ser Phe Gly Gly
                 85                  90                  95

Cys Leu Thr Gln Met Tyr Phe Met Ile Ala Leu Gly Asn Thr Asp Ser
            100                 105                 110

Tyr Ile Leu Ala Ala Met Ala Tyr Asp Arg Ala Val Ala Ile Ser Arg
            115                 120                 125

Pro Leu His Tyr Thr Thr Ile Met Ser Pro Arg Ser Cys Ile Trp Leu
130                 135                 140

Ile Ala Gly Ser Trp Val Ile Gly Asn Ala Asn Ala Leu Pro His Thr
145                 150                 155                 160

Leu Leu Thr Ala Ser Leu Ser Phe Cys Gly Asn Gln Glu Val Ala Asn
                165                 170                 175

Phe Tyr Cys Asp Ile Thr Pro Leu Leu Lys Leu Ser Cys Ser Asp Ile
            180                 185                 190

His Phe His Val Lys Met Met Tyr Leu Gly Val Gly Ile Phe Ser Val
            195                 200                 205

Pro Leu Leu Cys Ile Ile Val Ser Tyr Ile Arg Val Phe Ser Thr Val
210                 215                 220

Phe Gln Val Pro Ser Thr Lys Gly Val Leu Lys Ala Phe Ser Thr Cys
225                 230                 235                 240

Gly Ser His Leu Thr Val Val Ser Leu Tyr Tyr Gly Thr Val Met Gly
                245                 250                 255

Thr Tyr Phe Arg Pro Leu Thr Asn Tyr Ser Leu Lys Asp Ala Val Ile
            260                 265                 270

Thr Val Met Tyr Thr Ala Val Thr Pro Met Leu Asn Pro Phe Ile Tyr
            275                 280                 285

Ser Leu Arg Asn Arg Asp Met Lys Ala Ala Leu Arg Lys Leu Phe Asn
            290                 295                 300

Lys Arg Ile Ser Ser
305

<210> SEQ ID NO 12
<211> LENGTH: 381
<212> TYPE: PRT
<213> ORGANISM: Homo sapiens

<400> SEQUENCE: 12

Met Gly Cys Leu Gly Gly Asn Ser Lys Thr Thr Glu Asp Gln Gly Val
 1               5                  10                  15

Asp Glu Lys Glu Arg Arg Glu Ala Asn Lys Lys Ile Glu Lys Gln Leu
             20                  25                  30

Gln Lys Glu Arg Leu Ala Tyr Lys Ala Thr His Arg Leu Leu Leu Leu
         35                  40                  45

Gly Ala Gly Glu Ser Gly Lys Ser Thr Ile Val Lys Gln Met Arg Ile
 50                  55                  60

Leu His Val Asn Gly Phe Asn Pro Glu Glu Lys Lys Gln Lys Ile Leu
 65                  70                  75                  80

Asp Ile Arg Lys Asn Val Lys Asp Ala Ile Val Thr Ile Val Ser Ala
                 85                  90                  95

Met Ser Thr Ile Ile Pro Pro Val Pro Leu Ala Asn Pro Glu Asn Gln
            100                 105                 110

-continued

Phe Arg Ser Asp Tyr Ile Lys Ser Ile Ala Pro Ile Thr Asp Phe Glu
            115                 120                 125

Tyr Ser Gln Glu Phe Phe Asp His Val Lys Lys Leu Trp Asp Glu
    130                 135                 140

Gly Val Lys Ala Cys Phe Glu Arg Ser Asn Glu Tyr Gln Leu Ile Asp
145                 150                 155                 160

Cys Ala Gln Tyr Phe Leu Glu Arg Ile Asp Ser Val Ser Leu Val Asp
                165                 170                 175

Tyr Thr Pro Thr Asp Gln Asp Leu Leu Arg Cys Arg Val Leu Thr Ser
            180                 185                 190

Gly Ile Phe Glu Thr Arg Phe Gln Val Asp Lys Val Asn Phe His Met
        195                 200                 205

Phe Asp Val Gly Gly Gln Arg Asp Glu Arg Arg Lys Trp Ile Gln Cys
    210                 215                 220

Phe Asn Asp Val Thr Ala Ile Ile Tyr Val Ala Ala Cys Ser Ser Tyr
225                 230                 235                 240

Asn Met Val Ile Arg Glu Asp Asn Asn Thr Asn Arg Leu Arg Glu Ser
                245                 250                 255

Leu Asp Leu Phe Glu Ser Ile Trp Asn Asn Arg Trp Leu Arg Thr Ile
            260                 265                 270

Ser Ile Ile Leu Phe Leu Asn Lys Gln Asp Met Leu Ala Glu Lys Val
        275                 280                 285

Leu Ala Gly Lys Ser Lys Ile Glu Asp Tyr Phe Pro Glu Tyr Ala Asn
    290                 295                 300

Tyr Thr Val Pro Glu Asp Ala Thr Pro Asp Ala Gly Glu Asp Pro Lys
305                 310                 315                 320

Val Thr Arg Ala Lys Phe Phe Ile Arg Asp Leu Phe Leu Arg Ile Ser
                325                 330                 335

Thr Ala Thr Gly Asp Gly Lys His Tyr Cys Tyr Pro His Phe Thr Cys
            340                 345                 350

Ala Val Asp Thr Glu Asn Ile Arg Arg Val Phe Asn Asp Cys Arg Asp
        355                 360                 365

Ile Ile Gln Arg Met His Leu Lys Gln Tyr Glu Leu Leu
    370                 375                 380

<210> SEQ ID NO 13
<211> LENGTH: 340
<212> TYPE: PRT
<213> ORGANISM: Homo sapiens

<400> SEQUENCE: 13

Met Ser Glu Leu Glu Gln Leu Arg Gln Glu Ala Glu Gln Leu Arg Asn
1               5                   10                  15

Gln Ile Arg Asp Ala Arg Lys Ala Cys Gly Asp Ser Thr Leu Thr Gln
            20                  25                  30

Ile Thr Ala Gly Leu Asp Pro Val Gly Arg Ile Gln Met Arg Thr Arg
        35                  40                  45

Arg Thr Leu Arg Gly His Leu Ala Lys Ile Tyr Ala Met His Trp Gly
    50                  55                  60

Thr Asp Ser Arg Leu Leu Val Ser Ala Ser Gln Asp Gly Lys Leu Ile
65                  70                  75                  80

Ile Trp Asp Ser Tyr Thr Thr Asn Lys Val His Ala Ile Pro Leu Arg
                85                  90                  95

Ser Ser Trp Val Met Thr Cys Ala Tyr Ala Pro Ser Gly Asn Phe Val

```
                        100                 105                 110
Ala Cys Gly Gly Leu Asp Asn Ile Cys Ser Ile Tyr Ser Leu Lys Thr
            115                 120                 125

Arg Glu Gly Asn Val Arg Val Ser Arg Glu Leu Pro Gly His Thr Gly
        130                 135                 140

Tyr Leu Ser Cys Cys Arg Phe Leu Asp Asp Asn Gln Ile Ile Thr Ser
145                 150                 155                 160

Ser Gly Asp Thr Thr Cys Ala Leu Trp Asp Ile Glu Thr Gly Gln Gln
                165                 170                 175

Thr Val Gly Phe Ala Gly His Ser Gly Asp Val Met Ser Leu Ser Leu
            180                 185                 190

Ala Pro Asp Gly Arg Thr Phe Val Ser Gly Ala Cys Asp Ala Ser Ile
        195                 200                 205

Lys Leu Trp Asp Val Arg Asp Ser Met Cys Arg Gln Thr Phe Ile Gly
210                 215                 220

His Glu Ser Asp Ile Asn Ala Val Ala Phe Phe Pro Asn Gly Tyr Ala
225                 230                 235                 240

Phe Thr Thr Gly Ser Asp Asp Ala Thr Cys Arg Leu Phe Asp Leu Arg
                245                 250                 255

Ala Asp Gln Glu Leu Leu Met Tyr Ser His Asp Asn Ile Ile Cys Gly
            260                 265                 270

Ile Thr Ser Val Ala Phe Ser Arg Ser Gly Arg Leu Leu Leu Ala Gly
        275                 280                 285

Tyr Asp Asp Phe Asn Cys Asn Ile Trp Asp Ala Met Lys Gly Asp Arg
290                 295                 300

Ala Gly Val Leu Ala Gly His Asp Asn Arg Val Ser Cys Leu Gly Val
305                 310                 315                 320

Thr Asp Asp Gly Met Ala Val Ala Thr Gly Ser Trp Asp Ser Phe Leu
                325                 330                 335

Lys Ile Trp Asn
            340

<210> SEQ ID NO 14
<211> LENGTH: 68
<212> TYPE: PRT
<213> ORGANISM: Homo sapiens

<400> SEQUENCE: 14

Met Ser Gly Ser Ser Val Ala Ala Met Lys Lys Val Val Gln Gln
1               5                   10                  15

Leu Arg Leu Glu Ala Gly Leu Asn Arg Val Lys Val Ser Gln Ala Ala
            20                  25                  30

Ala Asp Leu Lys Gln Phe Cys Leu Gln Asn Ala Gln His Asp Pro Leu
        35                  40                  45

Leu Thr Gly Val Ser Ser Thr Asn Pro Phe Arg Pro Gln Lys Val
    50                  55                  60

Cys Ser Phe Leu
65

<210> SEQ ID NO 15
<211> LENGTH: 1144
<212> TYPE: PRT
<213> ORGANISM: Homo sapiens

<400> SEQUENCE: 15

Met Pro Arg Asn Gln Gly Phe Ser Glu Pro Glu Tyr Ser Ala Glu Tyr
```

```
1               5                   10                  15
Ser Ala Glu Tyr Ser Val Ser Leu Pro Ser Asp Pro Asp Arg Gly Val
            20                  25                  30
Gly Arg Thr His Glu Ile Ser Val Arg Asn Ser Gly Ser Cys Leu Cys
            35                  40                  45
Leu Pro Arg Phe Met Arg Leu Thr Phe Val Pro Glu Ser Leu Glu Asn
50                      55                  60
Leu Tyr Gln Thr Tyr Phe Lys Arg Gln Arg His Glu Thr Leu Leu Val
65                      70                  75                  80
Leu Val Val Phe Ala Ala Leu Phe Asp Cys Tyr Val Val Met Cys
            85                  90                  95
Ala Val Val Phe Ser Ser Asp Lys Leu Ala Ser Leu Ala Val Ala Gly
            100                 105                 110
Ile Gly Leu Val Leu Asp Ile Ile Leu Phe Val Leu Cys Lys Lys Gly
            115                 120                 125
Leu Leu Pro Asp Arg Val Thr Arg Arg Val Leu Pro Tyr Val Leu Trp
130                     135                 140
Leu Leu Ile Thr Ala Gln Ile Phe Ser Tyr Leu Gly Leu Asn Phe Ala
145                     150                 155                 160
Arg Ala His Ala Ala Ser Asp Thr Val Gly Trp Gln Val Phe Phe Val
            165                 170                 175
Phe Ser Phe Phe Ile Thr Leu Pro Leu Ser Leu Ser Pro Ile Val Ile
            180                 185                 190
Ile Ser Val Val Ser Cys Val Val His Thr Leu Val Leu Gly Val Thr
            195                 200                 205
Val Ala Gln Gln Gln Glu Glu Leu Lys Gly Met Gln Leu Leu Arg
210                     215                 220
Glu Ile Leu Ala Asn Val Phe Leu Tyr Leu Cys Ala Ile Ala Val Gly
225                     230                 235                 240
Ile Met Ser Tyr Tyr Met Ala Asp Arg Lys His Arg Lys Ala Phe Leu
            245                 250                 255
Glu Ala Arg Gln Ser Leu Glu Val Lys Met Asn Leu Glu Glu Gln Ser
            260                 265                 270
Gln Gln Gln Glu Asn Leu Met Leu Ser Ile Leu Pro Lys His Val Ala
            275                 280                 285
Asp Glu Met Leu Lys Asp Met Lys Lys Asp Glu Ser Gln Lys Asp Gln
            290                 295                 300
Gln Gln Phe Asn Thr Met Tyr Met Tyr Arg His Glu Asn Val Ser Ile
305                     310                 315                 320
Leu Phe Ala Asp Ile Val Gly Phe Thr Gln Leu Ser Ser Ala Cys Ser
            325                 330                 335
Ala Gln Glu Leu Val Lys Leu Leu Asn Glu Leu Phe Ala Arg Phe Asp
            340                 345                 350
Lys Leu Ala Ala Lys Tyr His Gln Leu Arg Ile Lys Ile Leu Gly Asp
            355                 360                 365
Cys Tyr Tyr Cys Ile Cys Gly Leu Pro Asp Tyr Arg Glu Asp His Ala
            370                 375                 380
Val Cys Ser Ile Leu Met Gly Leu Ala Met Val Glu Ala Ile Ser Tyr
385                     390                 395                 400
Val Arg Glu Lys Thr Lys Thr Gly Val Asp Met Arg Val Gly Val His
            405                 410                 415
Thr Gly Thr Val Leu Gly Gly Val Leu Gly Gln Lys Arg Trp Gln Tyr
            420                 425                 430
```

```
Asp Val Trp Ser Thr Asp Val Thr Val Ala Asn Lys Met Glu Ala Gly
        435                 440                 445

Gly Ile Pro Gly Arg Val His Ile Ser Gln Ser Thr Met Asp Cys Leu
        450                 455                 460

Lys Gly Glu Phe Asp Val Glu Pro Gly Asp Gly Gly Ser Arg Cys Asp
465                 470                 475                 480

Tyr Leu Glu Glu Lys Gly Ile Glu Thr Tyr Leu Ile Ile Ala Ser Lys
                485                 490                 495

Pro Glu Val Lys Lys Thr Ala Thr Gln Asn Gly Leu Asn Gly Ser Ala
                500                 505                 510

Leu Pro Asn Gly Ala Pro Ala Ser Ser Lys Ser Ser Pro Ala Leu
        515                 520                 525

Ile Glu Thr Lys Glu Pro Asn Gly Ser Ala His Ser Ser Gly Ser Thr
        530                 535                 540

Ser Glu Lys Pro Glu Glu Gln Asp Ala Gln Ala Asp Asn Pro Ser Phe
545                 550                 555                 560

Pro Asn Pro Arg Arg Arg Leu Arg Leu Gln Asp Leu Ala Asp Arg Val
                565                 570                 575

Val Asp Ala Ser Glu Asp Glu His Glu Leu Asn Gln Leu Leu Asn Glu
        580                 585                 590

Ala Leu Leu Glu Arg Glu Ser Ala Gln Val Val Lys Lys Arg Asn Thr
        595                 600                 605

Phe Leu Leu Ser Met Arg Phe Met Asp Pro Glu Met Glu Thr Arg Tyr
        610                 615                 620

Ser Val Glu Lys Glu Lys Gln Ser Gly Ala Ala Phe Ser Cys Ser Cys
625                 630                 635                 640

Val Val Leu Leu Cys Thr Ala Leu Val Glu Ile Leu Ile Asp Pro Trp
                645                 650                 655

Leu Met Thr Asn Tyr Val Thr Phe Met Val Gly Glu Ile Leu Leu Leu
                660                 665                 670

Ile Leu Thr Ile Cys Ser Leu Ala Ala Ile Phe Pro Arg Ala Phe Pro
        675                 680                 685

Lys Lys Leu Val Ala Phe Ser Thr Trp Ile Asp Arg Thr Arg Trp Ala
        690                 695                 700

Arg Asn Thr Trp Ala Met Leu Ala Ile Phe Ile Leu Val Met Ala Asn
705                 710                 715                 720

Val Val Asp Met Leu Ser Cys Leu Gln Tyr Tyr Thr Gly Pro Ser Asn
                725                 730                 735

Ala Thr Ala Gly Met Glu Thr Glu Gly Ser Cys Leu Glu Asn Pro Lys
                740                 745                 750

Tyr Tyr Asn Tyr Val Ala Val Leu Ser Leu Ile Ala Thr Ile Met Leu
                755                 760                 765

Val Gln Val Ser His Met Val Lys Leu Thr Leu Met Leu Leu Val Ala
        770                 775                 780

Gly Ala Val Ala Thr Ile Asn Leu Tyr Ala Trp Arg Pro Val Phe Asp
785                 790                 795                 800

Glu Tyr Asp His Lys Arg Phe Arg Glu His Asp Leu Pro Met Val Ala
                805                 810                 815

Leu Glu Gln Met Gln Gly Phe Asn Pro Gly Leu Asn Gly Thr Asp Arg
                820                 825                 830

Leu Pro Leu Val Pro Ser Lys Tyr Ser Met Thr Val Met Val Phe Leu
                835                 840                 845
```

-continued

```
Met Met Leu Ser Phe Tyr Tyr Phe Ser Arg His Val Glu Lys Leu Ala
850                 855                 860

Arg Thr Leu Phe Leu Trp Lys Ile Glu Val His Asp Gln Lys Glu Arg
865                 870                 875                 880

Val Tyr Glu Met Arg Arg Trp Asn Glu Ala Leu Val Thr Asn Met Leu
                885                 890                 895

Pro Glu His Val Ala Arg His Phe Leu Gly Ser Lys Lys Arg Asp Glu
            900                 905                 910

Glu Leu Tyr Ser Gln Thr Tyr Asp Glu Ile Gly Val Met Phe Ala Ser
        915                 920                 925

Leu Pro Asn Phe Ala Asp Phe Tyr Thr Glu Glu Ser Ile Asn Asn Gly
930                 935                 940

Gly Ile Glu Cys Leu Arg Phe Leu Asn Glu Ile Ile Ser Asp Phe Asp
945                 950                 955                 960

Ser Leu Leu Asp Asn Pro Lys Phe Arg Val Ile Thr Lys Ile Lys Thr
                965                 970                 975

Ile Gly Ser Thr Tyr Met Ala Ser Gly Val Thr Pro Asp Val Asn
            980                 985                 990

Thr Asn Gly Phe Ala Ser Ser Asn Lys Glu Asp Lys Ser Glu Arg Glu
        995                 1000                1005

Arg Trp Gln His Leu Ala Asp Leu Ala Asp Phe Ala Leu Ala Met
    1010                1015                1020

Lys Asp Thr Leu Thr Asn Ile Asn Asn Gln Ser Phe Asn Asn Phe
    1025                1030                1035

Met Leu Arg Ile Gly Met Asn Lys Gly Gly Val Leu Ala Gly Val
    1040                1045                1050

Ile Gly Ala Arg Lys Pro His Tyr Asp Ile Trp Gly Asn Thr Val
    1055                1060                1065

Asn Val Ala Ser Arg Met Glu Ser Thr Gly Val Met Gly Asn Ile
    1070                1075                1080

Gln Val Val Glu Glu Thr Gln Val Ile Leu Arg Glu Tyr Gly Phe
    1085                1090                1095

Arg Phe Val Arg Arg Gly Pro Ile Phe Val Lys Gly Lys Gly Glu
    1100                1105                1110

Leu Leu Thr Phe Phe Leu Lys Gly Arg Asp Lys Leu Ala Thr Phe
    1115                1120                1125

Pro Asn Gly Pro Ser Val Thr Leu Pro His Gln Val Val Asp Asn
    1130                1135                1140

Ser

<210> SEQ ID NO 16
<211> LENGTH: 1144
<212> TYPE: PRT
<213> ORGANISM: Homo sapiens

<400> SEQUENCE: 16

Met Pro Arg Asn Gln Gly Phe Ser Glu Pro Glu Tyr Ser Ala Glu Tyr
1               5                   10                  15

Ser Ala Glu Tyr Ser Val Ser Leu Pro Ser Asp Pro Asp Arg Gly Val
                20                  25                  30

Gly Arg Thr His Glu Ile Ser Val Arg Asn Ser Gly Ser Cys Leu Cys
            35                  40                  45

Leu Pro Arg Phe Met Arg Leu Thr Phe Val Pro Glu Ser Leu Glu Asn
        50                  55                  60
```

```
Leu Tyr Gln Thr Tyr Phe Lys Arg Gln Arg His Glu Thr Leu Leu Val
 65                  70                  75                  80

Leu Val Val Phe Ala Ala Leu Phe Asp Cys Tyr Val Val Met Cys
                 85                  90                  95

Ala Val Val Phe Ser Ser Asp Lys Leu Ala Ser Leu Ala Val Ala Gly
                100                 105                 110

Ile Gly Leu Val Leu Asp Ile Ile Leu Phe Val Leu Cys Lys Lys Gly
                115                 120                 125

Leu Leu Pro Asp Arg Val Thr Arg Arg Val Leu Pro Tyr Val Leu Trp
            130                 135                 140

Leu Leu Ile Thr Ala Gln Ile Phe Ser Tyr Leu Gly Leu Asn Phe Ala
145                 150                 155                 160

Arg Ala His Ala Ala Ser Asp Thr Val Gly Trp Gln Val Phe Phe Val
                165                 170                 175

Phe Ser Phe Phe Ile Thr Leu Pro Leu Ser Leu Ser Pro Ile Val Ile
                180                 185                 190

Ile Ser Val Val Ser Cys Val Val His Thr Leu Val Leu Gly Val Thr
            195                 200                 205

Val Ala Gln Gln Gln Gln Glu Glu Leu Lys Gly Met Gln Leu Leu Arg
210                 215                 220

Glu Ile Leu Ala Asn Val Phe Leu Tyr Leu Cys Ala Ile Ala Val Gly
225                 230                 235                 240

Ile Met Ser Tyr Tyr Met Ala Asp Arg Lys His Arg Lys Ala Phe Leu
                245                 250                 255

Glu Ala Arg Gln Ser Leu Glu Val Lys Met Asn Leu Glu Glu Gln Ser
                260                 265                 270

Gln Gln Gln Glu Asn Leu Met Leu Ser Ile Leu Pro Lys His Val Ala
            275                 280                 285

Asp Glu Met Leu Lys Asp Met Lys Lys Asp Glu Ser Gln Lys Asp Gln
                290                 295                 300

Gln Gln Phe Asn Thr Met Tyr Met Tyr Arg His Glu Asn Val Ser Ile
305                 310                 315                 320

Leu Phe Ala Asp Ile Val Gly Phe Thr Gln Leu Ser Ser Ala Cys Ser
                325                 330                 335

Ala Gln Glu Leu Val Lys Leu Leu Asn Glu Leu Phe Ala Arg Phe Asp
                340                 345                 350

Lys Leu Ala Ala Lys Tyr His Gln Leu Arg Ile Lys Ile Leu Gly Asp
            355                 360                 365

Cys Tyr Tyr Cys Ile Cys Gly Leu Pro Asp Tyr Arg Glu Asp His Ala
370                 375                 380

Val Cys Ser Ile Leu Met Gly Leu Ala Met Val Glu Ala Ile Ser Tyr
385                 390                 395                 400

Val Arg Glu Lys Thr Lys Thr Gly Val Asp Met Arg Val Gly Val His
                405                 410                 415

Thr Gly Thr Val Leu Gly Gly Val Leu Gly Gln Lys Arg Trp Gln Tyr
                420                 425                 430

Asp Val Trp Ser Thr Asp Val Thr Val Ala Asn Lys Met Glu Ala Gly
            435                 440                 445

Gly Ile Pro Gly Arg Val His Ile Ser Gln Ser Thr Met Asp Cys Leu
                450                 455                 460

Lys Gly Glu Phe Asp Val Glu Pro Gly Asp Gly Ser Arg Cys Asp
465                 470                 475                 480

Tyr Leu Glu Glu Lys Gly Ile Glu Thr Tyr Leu Ile Ile Ala Ser Lys
```

```
            485                 490                 495
Pro Glu Val Lys Lys Thr Ala Thr Gln Asn Gly Leu Asn Gly Ser Ala
            500                 505                 510

Leu Pro Asn Gly Ala Pro Ala Ser Ser Lys Ser Ser Ser Pro Ala Leu
            515                 520                 525

Ile Glu Thr Lys Glu Pro Asn Gly Ser Ala His Ser Ser Gly Ser Thr
            530                 535                 540

Ser Glu Lys Pro Glu Glu Gln Asp Ala Gln Ala Asp Asn Pro Ser Phe
545                 550                 555                 560

Pro Asn Pro Arg Arg Arg Leu Arg Leu Gln Asp Leu Ala Asp Arg Val
                    565                 570                 575

Val Asp Ala Ser Glu Asp Glu His Glu Leu Asn Gln Leu Leu Asn Glu
            580                 585                 590

Ala Leu Leu Glu Arg Glu Ser Ala Gln Val Val Lys Lys Arg Asn Thr
            595                 600                 605

Phe Leu Leu Ser Met Arg Phe Met Asp Pro Glu Met Glu Thr Arg Tyr
            610                 615                 620

Ser Val Glu Lys Glu Lys Gln Ser Gly Ala Ala Phe Ser Cys Ser Cys
625                 630                 635                 640

Val Val Leu Leu Cys Thr Ala Leu Val Glu Ile Leu Ile Asp Pro Trp
                    645                 650                 655

Leu Met Thr Asn Tyr Val Thr Phe Met Val Gly Glu Ile Leu Leu Leu
            660                 665                 670

Ile Leu Thr Ile Cys Ser Leu Ala Ala Ile Phe Pro Arg Ala Phe Pro
            675                 680                 685

Lys Lys Leu Val Ala Phe Ser Thr Trp Ile Asp Arg Thr Arg Trp Ala
            690                 695                 700

Arg Asn Thr Trp Ala Met Leu Ala Ile Phe Ile Leu Val Met Ala Asn
705                 710                 715                 720

Val Val Asp Met Leu Ser Cys Leu Gln Tyr Tyr Thr Gly Pro Ser Asn
                    725                 730                 735

Ala Thr Ala Gly Met Glu Thr Glu Gly Ser Cys Leu Glu Asn Pro Lys
            740                 745                 750

Tyr Tyr Asn Tyr Val Ala Val Leu Ser Leu Ile Ala Thr Ile Met Leu
            755                 760                 765

Val Gln Val Ser His Met Val Lys Leu Thr Leu Met Leu Leu Val Ala
            770                 775                 780

Gly Ala Val Ala Thr Ile Asn Leu Tyr Ala Trp Arg Pro Val Phe Asp
785                 790                 795                 800

Glu Tyr Asp His Lys Arg Phe Arg Glu His Asp Leu Pro Met Val Ala
                    805                 810                 815

Leu Glu Gln Met Gln Gly Phe Asn Pro Gly Leu Asn Gly Thr Asp Arg
            820                 825                 830

Leu Pro Leu Val Pro Ser Lys Tyr Ser Met Thr Val Met Val Phe Leu
            835                 840                 845

Met Met Leu Ser Phe Tyr Tyr Phe Ser Arg His Val Glu Lys Leu Ala
            850                 855                 860

Arg Thr Leu Phe Leu Trp Lys Ile Glu Val His Asp Gln Lys Glu Arg
865                 870                 875                 880

Val Tyr Glu Met Arg Arg Trp Asn Glu Ala Leu Val Thr Asn Met Leu
                    885                 890                 895

Pro Glu His Val Ala Arg His Phe Leu Gly Ser Lys Lys Arg Asp Glu
            900                 905                 910
```

```
Glu Leu Tyr Ser Gln Thr Tyr Asp Glu Ile Gly Val Met Phe Ala Ser
        915                 920                 925

Leu Pro Asn Phe Ala Asp Phe Tyr Thr Glu Glu Ser Ile Asn Asn Gly
    930                 935                 940

Gly Ile Glu Cys Leu Arg Phe Leu Asn Glu Ile Ile Ser Asp Phe Asp
945                 950                 955                 960

Ser Leu Leu Asp Asn Pro Lys Phe Arg Val Ile Thr Lys Ile Lys Thr
                965                 970                 975

Ile Gly Ser Thr Tyr Met Ala Ala Ser Gly Val Thr Pro Asp Val Asn
                980                 985                 990

Thr Asn Gly Phe Ala Ser Ser Asn Lys Glu Asp Lys Ser Glu Arg Glu
                995                 1000                1005

Arg Trp Gln His Leu Ala Asp Leu Ala Asp Phe Ala Leu Ala Met
    1010                1015                1020

Lys Asp Thr Leu Thr Asn Ile Asn Asn Gln Ser Phe Asn Asn Phe
    1025                1030                1035

Met Leu Arg Ile Gly Met Asn Lys Gly Gly Val Leu Ala Gly Val
    1040                1045                1050

Ile Gly Ala Arg Lys Pro His Tyr Asp Ile Trp Gly Asn Thr Val
    1055                1060                1065

Asn Val Ala Ser Arg Met Glu Ser Thr Gly Val Met Gly Asn Ile
    1070                1075                1080

Gln Val Val Glu Glu Thr Gln Val Ile Leu Arg Glu Tyr Gly Phe
    1085                1090                1095

Arg Phe Val Arg Arg Gly Pro Ile Phe Val Lys Gly Lys Gly Glu
    1100                1105                1110

Leu Leu Thr Phe Phe Leu Lys Gly Arg Asp Lys Leu Ala Thr Phe
    1115                1120                1125

Pro Asn Gly Pro Ser Val Thr Leu Pro His Gln Val Val Asp Asn
    1130                1135                1140

Ser

<210> SEQ ID NO 17
<211> LENGTH: 8
<212> TYPE: PRT
<213> ORGANISM: Artificial Sequence
<220> FEATURE:
<223> OTHER INFORMATION: FLAG tag sequence

<400> SEQUENCE: 17

Asp Tyr Lys Asp Asp Asp Asp Lys
1               5
```